(12) United States Patent
Kubu et al.

(10) Patent No.: US 7,951,534 B2
(45) Date of Patent: May 31, 2011

(54) HOT START NUCLEIC ACID AMPLIFICATION

(75) Inventors: Christopher James Kubu, Shaker Heights, OH (US); Jeannine Catherine Muller-Greven, Mentor, OH (US); Robert Bruce Moffett, Shaker Heights, OH (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 11/939,820

(22) Filed: Nov. 14, 2007

(65) Prior Publication Data

US 2008/0138878 A1    Jun. 12, 2008

Related U.S. Application Data

(62) Division of application No. 11/171,008, filed on Jun. 29, 2005.

(60) Provisional application No. 60/584,362, filed on Jun. 30, 2004.

(51) Int. Cl.
 *C12Q 1/68* (2006.01)
 *C12P 19/34* (2006.01)

(52) U.S. Cl. ......................... 435/6; 435/91.2

(58) Field of Classification Search .................. None
 See application file for complete search history.

(56) References Cited

U.S. PATENT DOCUMENTS

| | | | |
|---|---|---|---|
| 4,683,195 A | 7/1987 | Mullis et al. | |
| 4,889,818 A | 12/1989 | Gelfand et al. | |
| 4,965,188 A | 10/1990 | Mullis et al. | |
| 4,994,372 A | 2/1991 | Tabor et al. | |
| 5,223,414 A * | 6/1993 | Zarling et al. | 435/91.2 |
| 5,338,671 A | 8/1994 | Scalice et al. | |
| 5,364,790 A * | 11/1994 | Atwood et al. | 435/287.2 |
| 5,411,876 A | 5/1995 | Bloch et al. | |
| 5,449,603 A | 9/1995 | Nielson et al. | |
| 5,534,407 A * | 7/1996 | Tabor et al. | 435/5 |
| 5,538,871 A | 7/1996 | Nuovo et al. | |
| 5,605,824 A | 2/1997 | Nielson et al. | |
| 5,646,019 A * | 7/1997 | Nielson et al. | 435/91.5 |
| 5,677,152 A | 10/1997 | Birch et al. | |
| 5,773,257 A | 6/1998 | Nielson et al. | |
| 5,854,033 A | 12/1998 | Lizardi | |
| 6,124,120 A | 9/2000 | Lizardi | |
| 6,183,998 B1 | 2/2001 | Ivanov et al. | |
| 6,479,264 B1 | 11/2002 | Louwrier | |
| 6,642,034 B2 | 11/2003 | Lizardi | |
| 7,112,423 B2 | 9/2006 | Van Ness et al. | |
| 7,399,590 B2 * | 7/2008 | Piepenburg et al. | 435/6 |
| 2004/0058378 A1 | 3/2004 | Kong et al. | |
| 2004/0126789 A1 * | 7/2004 | Park et al. | 435/6 |
| 2005/0136443 A1 * | 6/2005 | Shigemori | 435/6 |
| 2005/0282176 A1 * | 12/2005 | Zhou et al. | 435/6 |

FOREIGN PATENT DOCUMENTS

| | | |
|---|---|---|
| EP | 0524808 A2 | 1/1993 |
| EP | 0863213 A1 | 9/1998 |
| EP | 0869187 A2 | 10/1998 |
| JP | H5-336971 A | 12/1993 |
| WO | WO 85/05685 | 12/1985 |
| WO | 91/06679 A1 | 5/1991 |
| WO | 2004/022770 A2 | 3/2004 |
| WO | WO2004/029292 * | 8/2004 |

OTHER PUBLICATIONS

Oshima et al. (Biotechniques, 1992, 13(2), p. 188).*
Perales et al. (Nucleic Acids Research, 2003, vol. 31, No. 22, p. 6473-6480).*
Kong et al. (JBC, 1997, vol. 272, No. 13, p. 8390-8397).*
He et al. (JBC, 2003, vol. 278, No. 32, p. 29538-29545).*
Lasham et al. (Molecular Cellular Probes, 1993, vol. 7, p. 67-73).*
Keating et al. (Biochemistry, 1988, vol. 27, p. 5240-5245).*
International Preliminary Report on Patentability for corresponding PCT application PCT/US2005/023824, dated May 26, 2008.
Written Opinion of the International Searching Authority for corresponding PCT application PCT/US2005/023824, dated Jan. 29, 2008.
International Search Report for corresponding PCT application PCT/US2005/023824, dated Jan. 29, 2008.
Daochun Kong, et al., "Role of the Bacteriophage T7 and T4 Single-stranded DNA-binding Proteins in the Formation of Joint Molecules and DNA Helicase-catalyzed Polar Branch Migration," Journal of Biological Chemistry, Mar. 28, 1997, vol. 272, No. 13, pp. 8390-8397.
Letter from Dr. Bruce Moffett to Steven J. Solomon, dated Oct. 24, 2005.
Robert G. Oshima, "Single-Stranded DNA Binding Protein Facilitates Amplification of Genomic Sequences by PCR," Biotechniques, Aug. 1992, 13(a), p. 188.
Celia Perales, et al., "Enhancement of DNA, cDNA synthesis and fidelity at high temperatures by a dimeric single-stranded DNA-binding protein," Nucleic Acids Research, 2003, vol. 31, No. 22, pp. 6473-6480.
C. Villalva, et al., "Increased Yield of PCR Products by Addition of T4 Gene 32 Protein to the SMART™ PCR cDNA Synthesis System," BioTechniques, Jul. 2001, vol. 31, No. 1, pp. 81-86.
Bruce M. Albets and Linda Frey, "T4 Bacteriophage Gene 32: A Structural Protein in the Replication and Recombination of DNA," Nature, vol. 227, pp. 1313-1318 (1970).
Kenneth R. Williams et al., "Limited Proteolysis Studies on the *Escherichia coli* Single-stranded DNA Binding Protein," J. Biol. Chem., vol. 258, No. 5, pp. 3346-3355.
Stephen R. Planck and Samuel H. Wilson, "Studies on the Structure of Mouse Helix-destabilizing Protein-1," J. Biol. Chem., vol. 255, No. 23, pp. 11547-11556 (1980).

(Continued)

*Primary Examiner* — Stephanie K Mummert
(74) *Attorney, Agent, or Firm* — Pearne & Gordon LLP

(57) ABSTRACT

Methods and compositions for performing nucleic acid duplication and amplification reactions are provided. A single-stranded nucleic acid binding protein is selected and provided in the reaction mixture which is assembled at a low, nonstringent temperature to include all of the necessary reagents for successful nucleic acid duplication or amplification reactions. By incorporating a single-stranded nucleic acid binding protein into the reaction mixture at low temperature, the generation of nonspecific products such as amplification products is improved despite the reaction mixture having been fully assembled at a nonstringent temperature.

9 Claims, 5 Drawing Sheets

OTHER PUBLICATIONS

Glenn Herrick and Bruce Alberts, "Nucleic Acid Helix-Coil Transitions Mediated by Helix-unwinding Proteins from Calf Thymus," J. Biol. Chem., vol. 251, No. 7, pp. 2133-2141 (1976).

Peter H. Von Heppel et al., "Molecular Approaches to the Interaction of Nucleic Acids with 'Melting" Proteins, Nucleic Acid-Protein Recognition, ed. H.J. Vogel, pp. 65-89, Academic Press, New York (1977).

Joseph E. Coleman and John L. Oakley, "Physical Chemical Studies of the Structure and Function of DNA Binding (Helix-Destabilizing) Proteins," CRC Crit. Rev. Biochem. Jan. 1980, pp. 247-289 (1980).

David E. Jensen et al., "DNA 'Melting Proteins," J. Biol. Chem., vol. 251, No. 22, pp. 7215-7228 (1976).

Benjamin Lewin, "The Topology of Nucleic Acids," Genes III, Chap. 3, pp. 57-63 (1987).

Wolfram Saenger, "Formation and Breakdown of Double-Helix Structure Show Cooperative Behavior," Principles of Nucleic Acid Structure, Chap. 6.8, pp. 141-149 (1983).

Peter H. Von Hippel et al., "Autoregulation of Gene Expression," J. Mol. Biol., vol. 162, pp. 795-818 (1982).

P. Kaspar et al., "An improved double stranded DNA sequencing method using gene 32 protein," Nucleic Acids Research, vol. 17, No. 9, p. 3616 (1989).

K. Muniyappa et al., "Mechanism of the concerted action of recA protein and helix-destabilizing proteins in homologous recombination," Proc. Natl. Acad. Sci., vol. 81, pp. 2757-2761 (1984).

G.F. Hong, "Sequencing of large double-stranded DNA using the dideoxy sequencing technique," Bioscience Reports 2, pp. 907-912 (1982).

Thomas A. Kunkel et al., "Single-strand binding protein enhances fidelity of DNA synthesis in vitro," Proc, Natl. Acad. Sci., vol. 16, No. 12, pp. 6331-6335 (1979).

Michael A. Innis et al., "DNA sequencing with *Thermus aquaticus* DNA polymerase and direct sequencing of polymerase chain reation-amplified DNA," Proc. Natl. Acad. Sci., vol. 85, pp. 9436-9440 (1988).

Marmur, J., Doty, P., "Determination of the Base Composition of Deoxyribonucleic Acid from its Thermal Denaturation Temperature", J. Mol. Biol., 1962, vol. 5, pp. 109-118.

Suggs, et al., "Use of Synthetic Oligodeoxyribonucleotides for the Isolation of Specific Cloned DNA Sequences," Developmental Biology Using Purified Genes, Brown, D., ed., ICN-UCLA Symposia on Molecular and Cellular Biology, 1981, vol. XXIII, pp. 683-693.

Saiki, et al., "Primer-Directed Enzymatic Amplification of DNA with a Thermostable DNA Polymerase", Science, 1988, vol. 239, pp. 487-491.

Dunn, J., et al., "Complete Nucleotide Sequence of Bacteriophage T7 DNA and the Locations of T7 Genetic Elements", J. Mol. Biol., 1963, vol. 166, pp. 477-535.

Scherzinger, E, et al., "Stimulation of T7 DNA Polymerase by a New Phage-Coded Protein", Molec. Gen. Genet., 1973, vol. 123, pp. 247-262.

Chase, J. Williams, K, "Single-Stranded DNA Binding Proteins Required for DNA Replication", Ann. Rev. Biochem., 1986, vol. 55, pp. 103-136.

Chien, A., et al., "Deoxyribonucleic Acid Polymerase from the Extreme Thermophile *Thermus aquaticus*", J. Bacterial., 1976, vol. 127, No. 3, pp. 1550-1557.

Chou, Q., et al., "Prevention of pre-PCR mis-priming and primer dimerization improves low-copy number amplifications", Nuc. Acids Res., 1992, vol. 20, No. 7, pp. 1717-1723.

Curth, U., et al., "In vitro and in vivo function of the C-terminus of *Escherichia coli* single-stranded DNA binding protein", Nuc. Acids Res., 1996, vol. 24, No. 14, pp. 2706-2711.

Gillam, S., et al., "The base-paring specificity of cellulos-pdT9", Nuc. Acids Res., 1975, vol. 2, pp. 625-634.

He, et al., "The Carboxyl-terminal Domain of Bacteriophage T7 Single-stranded DNA-binding Protein Modulates DNA Binding and Interaction with T7 DNA Polymerase", J. Biol. Chem., 2003, vol. 278, No. 32, pp. 29538-29545.

Hollis, T., et al., "Structure of the gene 2.5 protein, a single-stranded DNA binding protein encoded by bacteriophage T7", Proc. Nat'l. Acad. Sci. USA, 2001, vol. 98, No. 17, pp. 9557-9562.

Hyland, et al., "The DNA Binding Domain of the Gene 2.5 Single-stranded DNA-binding Protein of Bacteriophage T7", J Biol. Chem., 2003, vol. 278, No. 9, pp. 7247-7256.

Kim, Y., et al., "Purification and Characterization of the Bacteriophage T7 Gene 2.5 Protein", J Biol. Chem., 1992, vol. 267, No. 21, pp. 15022-15031.

Lindberg, G., et al., "Purification and Characterization of the Coliphage N4-coded Single-stranded DNA Binding Protein", J. Biol. Chem., 1989, vol. 264, No. 21, pp. 12700-12708.

Reuben, R., Gefter, M., A DNA-Binding Protein Induced by Bacteriophage T7:, Proc. Natl. Acad. Sci. USA, 1973, vol. 70, No. 6, pp. 1846-1850.

Rezende, L., et al., "Essential Amino Acid Residues in the Single-stranded DNA-binding Protein of Bacteriophage T7", J. Biol. Chem., 2002, vol. 277, No. 52, pp. 50643-50653.

Wallace, R., et al., "Hybridization of synthetic oligodeoxyribonucleotides to x 174 DNA: the effect of single base pair mismatch", Nuc. Acids Res., 1979, vol. 6, No. 11, gs. 3543-3557.

Slawomir Dabrowski et al., "Novel thermostable ssDNA-binding proteins from *Thermus thermophilus* and *T. aquatius*—expression and purification," Protein Expression and Purification, vol. 26, pp. 131-138 (2002).

Quin Chou, "Minimizing deletion mutagenesis artifact during Taq DNA polymerase PCR by *E. coli* SSB," Nucleic Acids Research, vol. 20, No. 16, pp. 4371 (1992).

Klaus Schwarz et al., "Improved yields of long PCR products using gene 32 protein," Nucleic Acids Research, vol. 18, No. 4, pp. 1079 (1990).

Michael Panaccio and Andrew Lew, "PCR based diagnosis in the presence of 8% (v/v) blood," Nucleic Acids Research, vol. 19, No. 5, pp. 1151 (1991).

Waleed Abu Al-Soud and Peter Radstrom, "Effects of Amplification Facilitators on Diagnostic PCR in the Presence of Blood, Feces, and Meat," Journal of Clinical Microbiology, vol. 2, pp. 295-298 (1994).

Ralph Rapley, "Enhancing PCR Amplification and Sequencing Using DNA-Binding Proteins," Molecular Biotechnology, vol. 2, pp. 295-298 (1994).

Dharambir K. Sandhu and Phouthone Keohavong, "Effects of the T4 bacteriophage gene 32 product on the efficiency and fidelity of DNA amplification using T4 DNA polymerase," Gene, vol. 144, pp. 53-58 (1994).

Annette Lasham and Mark G. Darlison, "Direct sequencing of lambda DNA from crude lysate using an improved linear amplification technique," Molecular and Cellular Probes, vol. 7, pp. 67-73 (1993).

Maria Ehn et al., :*Escherichia coli* single-stranded DNA-binding protein, a molecular tool for improved sequence quality in pyrosequencing, Electrophoresis, vol. 23, pp. 3289-3299 (2002).

Anthony A. Oliva, Jr. and John W. Swann, "Increased Yield of PCR Products by Addition of T4 Gene 32 Protein to the SMART™ PCR cDNA Synthesis System," BioTechniques, vol. 258, No. 20, pp. 12274-12279 (1983).

Michael D. Topal and Navin K. Sinha, "Products of Bacteriophage T4 Genes 32 and 45 Improve the Accurancy of DNA Replication in Vitro," The Journal of Biological Chemistry, vol. 258, No. 20, pp. 12274-12279 (1983).

Slawomir Dabrowski and Jozef Kur, "Cloning, Overexpression, and Purification of the Recombinant His-Tagged SSB Protein of *Escherichia coli* and Use in Polymerase Chain Reaction Amplification," Protein Expression and Purification, vol. 16, pp. 96-102 (1999).

Supplementary European Search Report from corresponding European application serial No. 05764400.7.

Keating, K. M. et al., "Thermal Denaturation of T4 Gene 32 Protein: Effects of Zinc Removal and Substitution," Biochemistry, 1988, vol. 27, p. 5240-5245.

Lizardi, P.M. et al., "Mutation detection and single-molecule counting using isothermal rolling-circle amplification," Nature Genetics, Jul. 1998, vol. 19, p. 225-232.

Waleed Abu Al-Soud and Peter Radstrom, "Effects of Amplification Facilitators on Diagnostic PCR in the Presence of Blood, Feces and Meat," Journal of Clinical Microbiology, vol. 38, No. 12, p. 4463-4470 (2000).

Rigler, M.N. and Romano, L.J, "Differences in the mechanism of stimulation of T7 DNA polymerase by two binding modes of *Escherichia coli* single-stranding DNA-binding protein," Journal of Biological Chemistry, vol. 270, No. 15, pp. 8910-8919, 1995.

Office action dated Sep. 14, 2009, issued in corresponding European Patent Application No. 05764400.7.

* cited by examiner

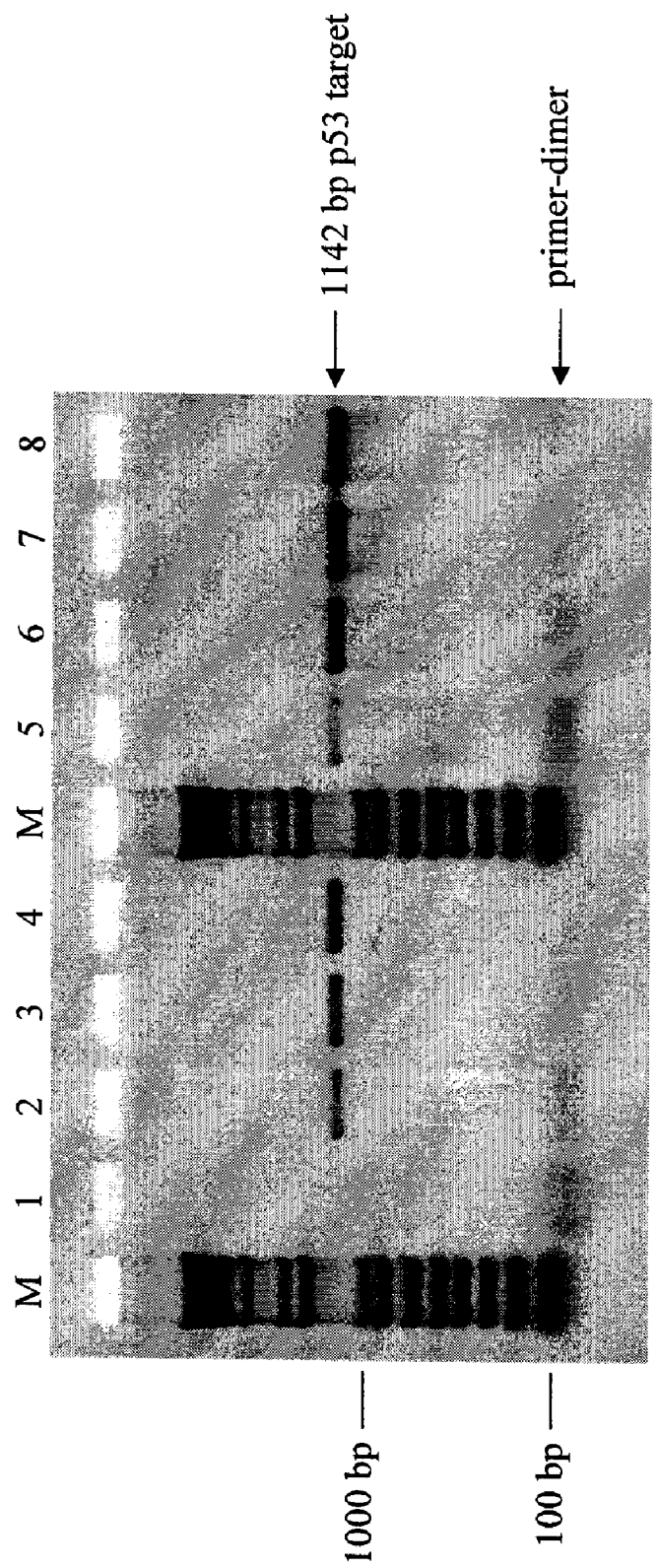

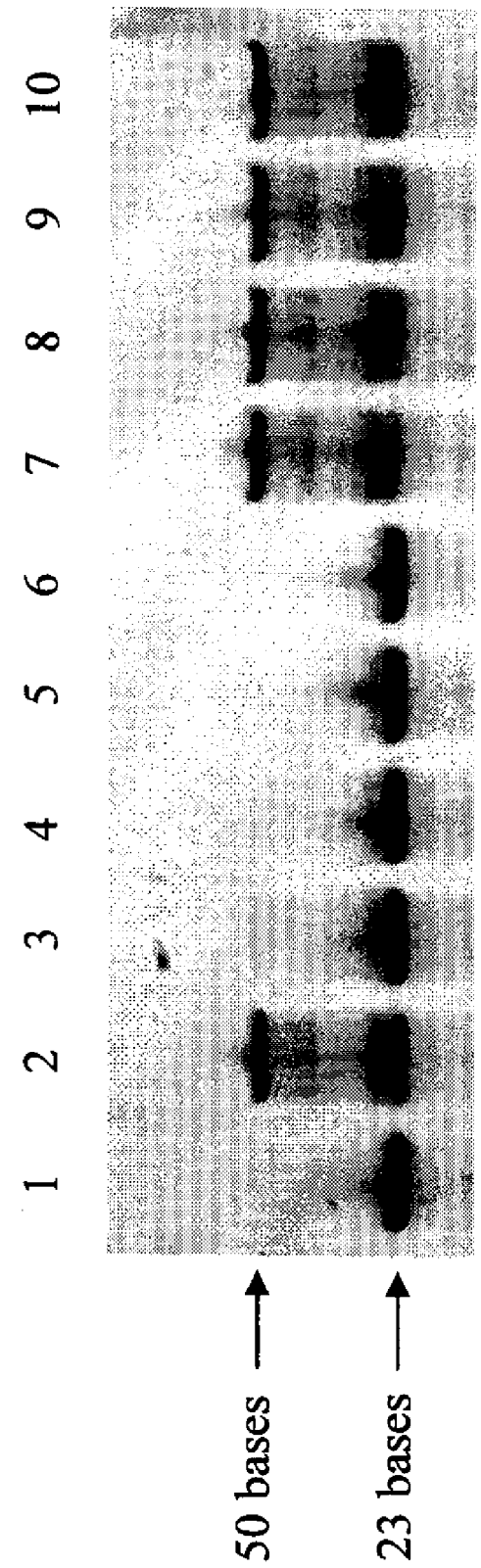

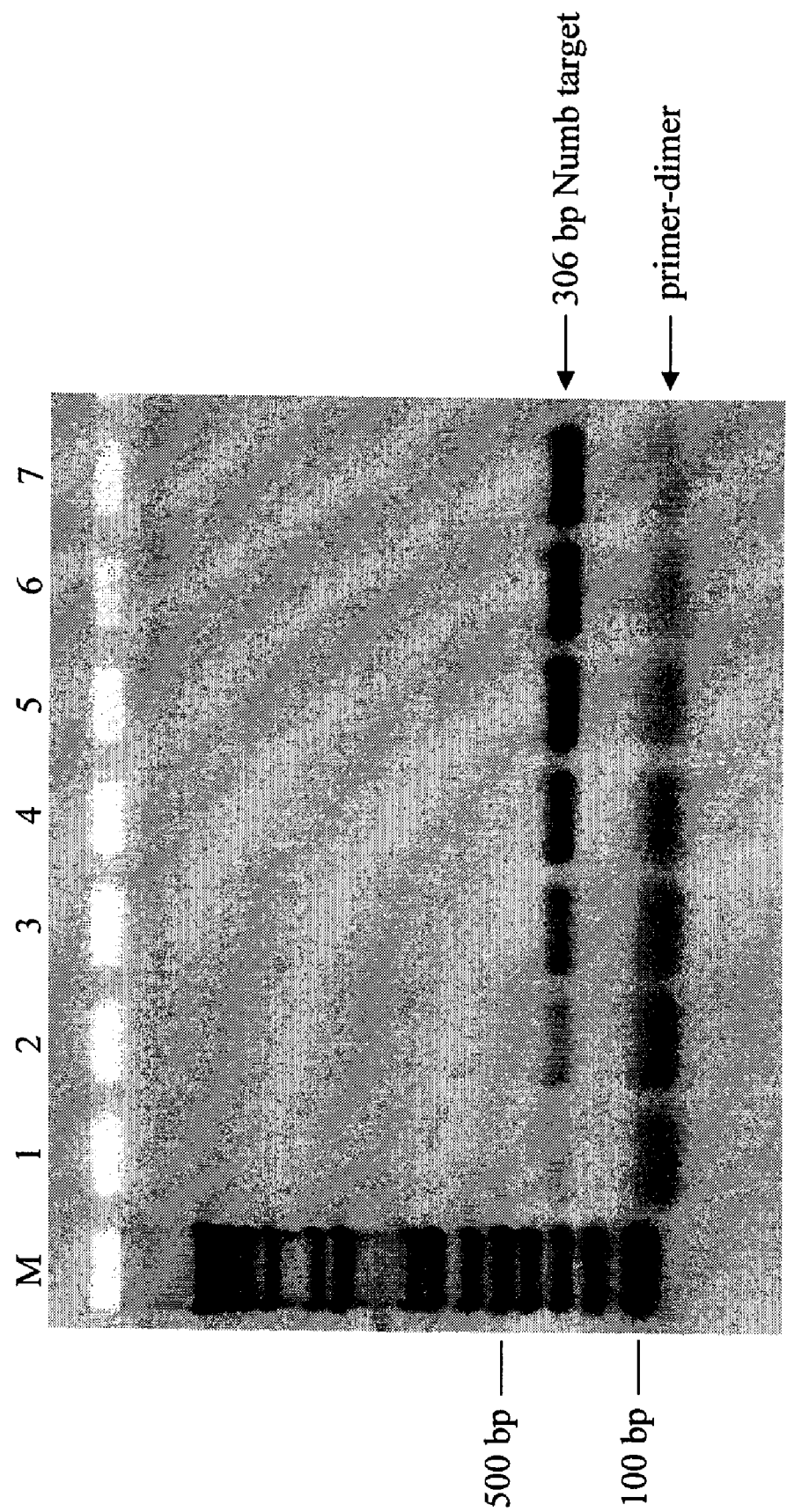

HOT START NUCLEIC ACID AMPLIFICATION

This application is a divisional of co-pending application Ser. No. 11/171,008 filed Jun. 29, 2005, which claims the benefit of U.S. provisional patent application Ser. No. 60/584,362 filed Jun. 30, 2004, the contents of each of which are incorporated herein by reference in their entirety.

BACKGROUND OF THE INVENTION

1. Field of Invention

The present invention provides a method that reduces or eliminates nonspecific primer extension products. More specifically, the method uses single-stranded nucleic acid binding proteins to reduce or eliminate these products. This invention is contemplated to be especially useful as a novel Hot Start method for the polymerase chain reaction (PCR).

2. Description of Related Art

Amplification of nucleic acids is of fundamental importance in modern science. During this process, nucleic acids are duplicated or replicated through coordinated, catalytic synthesis.

In general, nucleic acid amplification occurs through a process of hybridizing (annealing or pairing) a relatively short single-stranded nucleic acid (primer or oligonucleotide), to a relatively longer single-stranded nucleic acid counterpart (target or template) that has complementary nucleic acid sequence. Complementary annealing refers to the base pairs which form and are stabilized by hydrogen bonds described by Watson-Crick pairing rules (i.e., A-T and G-C base pairs). A polymerase can use this hybrid (or complement) to catalytically add bases or nucleotides which are present in the reaction to the 3' end of the primer. The nucleotides are added such that they are complementary to the target or template. Since the newly synthesized strand of nucleic acid is the result of nucleotides which extend the length of the primer, this process is also known as primer extension. To be extended by a polymerase, a primer strand first must be annealed to a template strand.

Although the primer(s) used in primer extension reactions are designed to be complementary to a specific portion of the template strand, under certain conditions the primer can and will anneal to other regions of the template strand with which it is only partially complementary, or in rare cases, non-complementary. As used herein, a fully complementary pairing is referred to as and is the result of specific priming and a partially complementary (or noncomplementary) pairing is referred to as and is the result of nonspecific priming. Since the polymerase cannot discriminate between partial versus full complements, primer extension products can and will be formed from both if both are present under extension conditions. As used herein, primer extension products from full complements are referred to as specific products and those from partial (or non-) complements are referred to as nonspecific products.

The degree to which a primer will hybridize to full versus partial (or non-) complementary sequences is governed by well-known principles of thermodynamics. A useful parameter is known as the melting temperature ($T_m$) and is defined as the temperature at which 50% of the primer and its true complement or intended target sequence is annealed. The most common method to determine the actual $T_m$ is to plot temperature versus absorbance in a UV spectrophotometer (e.g., Marmur and Doty, 1962, *Journal of Molecular Biology* 5:109-118). This empirical determination is often not practical and thus theoretical methods have been devised to predict melting temperatures. One such method is through an equation known as the Wallace Rule (Suggs et al., 1981, In *Developmental Biology using Purified Genes* 23:683-693). This equation states that $T_m$ (in ° C.) is approximately equal to $2\times(\#A+\#T)+4\times(\#G+\#C)$, where # is the number of A, G, C, or T bases present in the primer. Thus, a primer 20 bases long with an equal base content would be predicted to have a $T_m$ of $2\times(5+5)+4\times(5+5)=60°$ C.

Although other factors such as salt concentration, DNA concentration, and the presence of denaturants affect the melting temperature, the main contribution to $T_m$ is from the length and base composition of the primer. Given a defined primer sequence, the temperature of the hybridization reaction determines the amount of specific versus nonspecific priming based on thermodynamic principles. Temperatures significantly below the $T_m$ will permit nonspecific priming while temperatures significantly above the $T_m$ will restrict nonspecific and specific priming (e.g., Gillam et al., 1975, *Nucleic Acids Research* 2(5):625-634; Wallace et al., 1979, *Nucleic Acids Research* 6(11):3543-3557). Ideally, hybridization is carried out at or near the $T_m$ of the primer(s) to generate specific complements and thus specific primer extension products. As used herein, hybridization and primer extension temperatures significantly lower than the $T_m$ of the primers are referred to as permissive or nonstringent while temperatures at or near the $T_m$ are referred to as restrictive or stringent. Thus, permissive or nonstringent temperatures lead to nonspecific primer extension products while restrictive or stringent temperatures lead to specific ones.

A well-known example of primer extension is the polymerase chain reaction (PCR). In this technique, DNA synthesis occurs in a series of steps comprising a cycle, this cycle being repeated many times to amplify the primer extension reaction products for further analyses. Two primers typically are used in which their respective 3'-ends face one another to generate a double-stranded DNA product whose length is defined as the distance between the primers. Typically, the cycle consists of a step which generates single-stranded DNA, a step which allows primers to hybridize with their target sequences, and a subsequent step for primer extension by the polymerase. The PCR technique is described in detail in U.S. Pats. Nos. 4,683,202; 4,683,195; and 4,965,188. A variant of PCR, which is called reverse transcription-PCR (RT-PCR), is when RNA is used as a template in the reaction instead of DNA. In this technique, an initial step of converting the RNA template to DNA is performed with a polymerase which has reverse transcriptase activity. Following this initial template conversion (reverse transcription step), reactions proceed as in standard PCR.

Each cycle of PCR generates a geometric expansion of the original target (i.e., doubling per cycle), which after the 25-50 cycles typically employed in PCR can amplify the target well over a billion times. Unfortunately, amplification from non-specific priming can also occur which is detrimental since these nonspecific products may obscure specific ones. The specificity of the PCR depends on many factors, but as previously discussed, the temperature of the hybridization and subsequent extension steps is important in obtaining specific primer extension products. Fortunately, the discovery and widespread use of thermostable polymerases, such as the polymerase from *Thermus aquaticus* (Taq DNA Polymerase), allows the use of more stringent reaction temperatures (Chien et al., 1976, *Journal of Bacteriology* 127(3): 1550-1557; Saiki et al., 1988, *Science* 239(4839):487-491). Stringent hybridization temperatures increase the probability of generating specific products.

Although the temperatures used during the polymerase chain reaction can be stringent, the reaction mixtures themselves are not conveniently assembled at higher temperatures, temperatures at which greater priming specificity occurs. PCR reactions are usually assembled at lower temperatures such as on ice or most preferably at room temperature (i.e., 20-25° C.). If the average primer can be assumed to have a $T_m$ of about 50-60° C., the temperatures at which reaction set-up occur are clearly significantly lower and will favor nonspecific priming. At room temperature, the conventional polymerases used in the PCR (e.g., Taq DNA Polymerase) have some degree of catalytic activity which leads to the synthesis of nonspecific reaction products. In addition, even if the reactions are assembled on ice, they must be placed in a machine which provides the temperatures necessary for cycling. Stringent hybridization temperatures higher than ice cannot be achieved instantaneously and nonspecific products can also be generated during this "ramping" stage. At permissive temperatures primers not only pair nonspecifically with the template but also pair with other primers leading to nonspecific primer extension products known as "primer-dimers." Nonspecific amplification is a ubiquitous problem during the assembly of polymerase chain reactions and is covered in greater detail in Chou et al., 1992, *Nucleic Acids Research* 20(7):1717-1723.

Since nonspecific amplification products can be generated during assembly of PCR reactions, a method is needed that can reduce or eliminate these artifacts. Various methods have been developed to address this problem. These techniques are generally known as "hot-start" methods because the primer extension reactions are not allowed to "start" until stringent or "hot" hybridization temperatures have been reached. Several of these methods are briefly described below.

In the simplest hot-start method, one of the critical components for successful DNA synthesis is omitted from the reaction mixture during preparation at room temperature. Then, the omitted component is added manually, as through pipetting, after the temperature of the reaction mixture has reached, or more usually exceeded, a threshold stringent temperature based upon the $T_m$ of the primer(s). This method is often called manual hot-start PCR. For example, one may omit the polymerase or the divalent cation (e.g., $Mg^{2+}$) which is essential for polymerase activity from the reaction mixture until the stringent temperature is reached or exceeded. Because a key component is unavailable at lower temperatures, nonspecific extension products cannot be formed. This method is tedious and cumbersome when multiple reactions are performed and also can lead to contamination of PCR reactions since tubes in close proximity to one another must be opened and closed manually by the operator in order to introduce the omitted component.

In another hot-start method, all of the necessary components are assembled in the reaction mixture at room temperature, but one critical component is physically isolated from the remainder of the reaction mixture using a barrier material that will melt or dissolve at elevated temperatures. Once the barrier material, typically a wax, has melted, the isolated component is introduced into the remainder of the reaction mixture and the primer extension reaction can proceed at the more stringent temperature. Conventionally, the polymerase is isolated using the barrier or wax material. This method, which is described in detail in U.S. Pat. No. 5,411,876 and Chou et al., *Nucleic Acids Research* 20(7):1717-1723 (1992), allows more specific amplification but is cumbersome in the set-up and implementation of the barrier material.

Another method is to use an antibody that non-covalently binds to the polymerase and prevents its activity at lower temperatures. At higher temperatures, the non-covalent bond between the antibody and the polymerase is disrupted and polymerase activity is restored for the rest of the PCR reaction. This method is further described in U.S. Pat. No. 5,338,671. Although this method is effective, the production process for generating the antibody is expensive and can introduce contaminating mammalian genomic DNA into the PCR reaction.

Yet another technique involves covalent attachment of a chemical moiety to the polymerase which blocks its activity at lower temperatures. This covalent bond can be broken after significant heating (e.g., above 95° C. for about 10-15 minutes) after which the polymerase activity is restored. A variety of chemical modifications can be introduced to produce the polymerase-moiety complex required to practice this technique as described in U.S. Pats. Nos. 5,677,152, 6,183,998 and 6,479,264. This technique has the disadvantage of requiring an extensive initial heating step which can damage DNA through heat-induced depurination. Such an extensive heating step also markedly reduces the activity of the polymerase relative to standard PCR methods.

In summary, primer extension reactions can be defined by two key events. One, the process of hybridizing the primer to the template and two, the extension of the hybrid by the catalytic action of a polymerase. The specificity of the hybridization is governed by the principles of thermodynamics in which lower temperatures favor nonspecific priming and amplification artifacts. Because polymerase chain reactions are conventionally assembled at lower temperatures, amplification artifacts can be a problem. Various methods have been developed to address this problem, techniques known as hot-start PCR. The present invention is a novel method of hot-start PCR.

SUMMARY OF THE INVENTION

A method of duplicating a template nucleic acid, or a portion thereof, is provided wherein a primer having a nucleotide sequence that is complementary to a target portion of the template nucleic acid is hybridized to the template nucleic acid and then extended via an enzyme. The method includes the following steps: (a) at a first temperature, preparing a reaction mixture including a primer, a template nucleic acid, an enzyme effective to catalyze primer extension and an effective amount of single-stranded nucleic acid binding protein, (b) at a second temperature higher than the first temperature, carrying out a hybridization reaction to produce a hybridized product, and (c) at a third temperature higher than the first temperature, carrying out a primer extension reaction to produce from the hybridized product an extended product; wherein the generation of specific extended product is improved as a result of incorporating the single-stranded nucleic acid binding protein into the reaction mixture at the first temperature.

A primer complex also is provided. The complex includes a primer having a nucleotide sequence that is complementary to a specific target portion of a template nucleic acid molecule, and a single-stranded nucleic acid binding protein interacting with the primer. The single-stranded nucleic acid binding protein is selected such that 1) it in effect inhibits the primer from participating in a primer extension reaction up to at least a first temperature at or below 30° C., and 2) that interaction ceases or is disrupted at a second temperature in the range of 30° C. to about 72° C. such that the primer is substantially uninhibited by the single-stranded nucleic acid binding protein from participating in a primer extension reaction at the second temperature.

A PCR reaction mixture also is provided, including a primer having a nucleotide sequence that is complementary to a specific target portion of a template nucleic acid, and a single-stranded nucleic acid binding protein effective to inhibit the primer from participating in a primer extension reaction up to at least a first temperature at or below 30° C., wherein the inhibitive capability of the single-stranded nucleic acid binding protein is lost at a second temperature in the range of 30° C. to about 72° C.

BRIEF DESCRIPTION OF THE DRAWINGS

FIG. 2 is an agarose gel electrophoresis image illustrating the effectiveness of hot-start methods using a mixture of wild-type and the Δ26C mutant of T7 SSB, T7 gp2.5-Δ26C, as described in Example 2.

FIG. 3b is a denaturing, polyacrylamide gel electrophoresis image illustrating the blocking effects of a mixture of wild-type and the Δ26C mutant of T7 SSB in the mock PCR reaction described in Example 3.

FIG. 4 is an agarose gel electrophoresis image illustrating a range of concentrations of wild-type T7 SSB that are effective in a hot-start method as herein described, Example 4.

DETAILED DESCRIPTION OF PREFERRED EMBODIMENTS OF THE INVENTION

Figure 1:
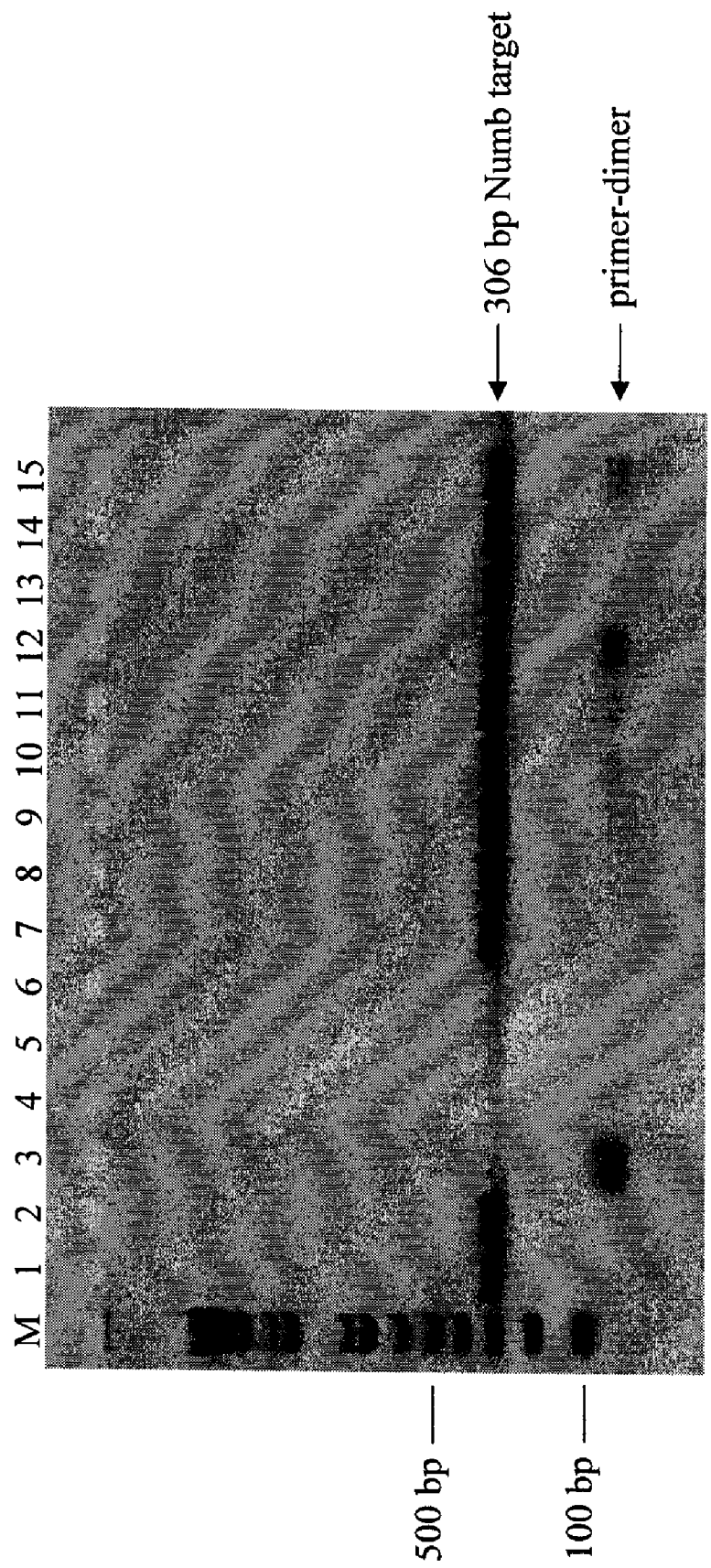
FIG. 1 is an agarose gel electrophoresis image illustrating the effectiveness of hot-start methods using single-stranded DNA binding proteins according to the disclosed methods, compared to other methods as described in Example 1.

As used herein, when a range such as 5-25 (or 5 to 25) is given, this means preferably at least 5 and, separately and independently, preferably not more than 25.

Also as used herein, a 'single-stranded nucleic acid binding protein' (SSB or SSBs when plural) is a polypeptide or protein that exhibits very high affinity for interacting with (i.e., binding) single-stranded nucleic acids. Typically, a single-stranded nucleic acid binding protein exhibits a higher affinity for and preferentially binds to single-stranded nucleic acids over double-stranded nucleic acids. SSBs can bind to a single-stranded molecule or fragment of DNA or RNA, but generally a specific type of SSB prefers one to the other. The SSB proteins discussed herein have a higher affinity for DNA than for RNA, and are more often referred to as single-stranded DNA binding proteins in the scientific literature. SSBs bind to single-stranded nucleic acids stoichiometrically, which means that they bind in approximately fixed molar ratios with respect to the nucleic acid. In addition, SSBs generally bind nucleic acid with no sequence specificity (i.e., without regard to the base composition of the nucleic acid). The SSBs referred to herein are not enzymes, meaning they do not exhibit any substantial (or known) enzymatic activity (Chase and Williams, 1986, *Annual Reviews of Biochemistry* 55:103-136).

Also as used herein, the term 'hybridization' refers to the bonding of one single-stranded nucleic acid to another single-stranded nucleic acid, such as a primer strand to a template strand, via hydrogen bonds between complementary Watson-Crick bases in the respective single-strands to thereby generate a double-stranded nucleic acid hybrid or complex as otherwise known in the art. Commonly, the terms 'hybridize,' 'anneal,' and 'pair' are used interchangeably in the art to describe this reaction, and so too they are used interchangeably herein. Hybridization may proceed between two single-stranded DNA molecules, two single-stranded RNA molecules, or between single-strands of DNA and RNA, to form a double-stranded nucleic acid complex.

Also as used herein, the term 'denaturation' means the process of separating double-stranded nucleic acids to generate single-stranded nucleic acids. This process is also referred to as 'melting'. The denaturation of double-stranded nucleic acids can be achieved by various methods, but herein it principally is carried out by heating.

Also as used herein, the term 'single-stranded DNA' will often be abbreviated as 'ssDNA', the term 'double-stranded DNA' will often be abbreviated as 'dsDNA', and the term 'double-stranded RNA' will often be abbreviated as 'dsRNA'. It is implicit herein that the term 'RNA' refers to the general state of RNA which is single-stranded unless otherwise indicated.

Also as used herein, an SSB is said to 'interact' or to be 'interacting' with a primer when it cooperates with, or otherwise is correlated, associated, coupled or otherwise complexed to, the primer in such a manner so as to substantially inhibit or prevent the primer from participating in a primer extension reaction. The term 'interact' and variants thereof is/are considered to include, but not necessarily to be limited to, a chemical bond (covalent, non-covalent or otherwise) as well as other modes of binding or bonding that are or may be achieved between an SSB and its associated primer so as to produce the primer extension-inhibitive effect described in this paragraph, and further described herein as well as observed in the following Examples.

The present invention provides methods and reagents that inhibit or prevent the generation of nonspecific primer extension products that result from nonspecific priming events at permissive temperatures. The methods are envisioned to be particularly useful and applicable to primer extension via the polymerase chain reaction (PCR) although the invention is not limited to such reactions. The present invention is applicable to any reaction or process incorporating otherwise conventional hybridization and primer extension reactions to produce an amplified or newly synthesized double-stranded product from a primer-template hybrid, whether as an intermediate or final product. As such, the present invention would also be useful for the variation of PCR called reverse transcription-PCR in which a reverse transcription step converts RNA to DNA. Other examples of primer extension reactions include DNA and RNA sequencing, reverse transcription, in vitro transcription and isothermal amplification, among others.

PCR mixtures usually are prepared or assembled at room temperature (less than 30° C., more typically 20-25° C.) or on ice (0° C.) in reaction tubes suitable for accommodating the hybridization and primer extension reactions in a conventional thermal cycler. Nearly, if not entirely, all PCR mixtures initially are prepared below 37° C. A typical PCR mixture will include at least the following essential components:

a template nucleic acid, which can be single-stranded or double-stranded, which it is desired to amplify;

at least one primer that is complementary to a target portion of the template nucleic acid—if the template is double-stranded and it is desired to amplify both strands then at least two primers will be provided, each being complementary to a specific target portion on each of the sense and anti-sense template strands;

the four deoxyribonucleotides necessary for enzyme-directed nucleic acid synthesis (dATP, dGTP, dTTP and dCTP), occasionally exogenous nucleotides may be included as well (e.g., dUTP);

an enzyme or enzymes for directing nucleic acid synthesis, typically a polymerase such as Taq DNA polymerase and/or other thermostable polymerases, reverse transcriptase (e.g., MMLV-RT or AMV-RT) or other suitable enzyme if template is RNA;

where a polymerase(s) is used, a divalent cation such as $Mg^{2+}$, $Mn^{2+}$, etc., which is an accessory for polymerase activity;

a suitable reaction buffer solution capable of supporting the cyclic hybridization and primer extension reactions as further described below.

All of the foregoing components are conventional for PCR (and RT-PCR) and the amounts of each (as well as compositions for the reaction buffer solution) are well known or ascertainable to those having ordinary skill in the art without undue experimentation. Accordingly, they will not be further described here except to note that in conventional hot-start PCR techniques such as those described in the BACKGROUND section, at least one of the foregoing essential components, typically the polymerase(s), is withheld or isolated from the remaining mixture until a stringent hybridization temperature has been reached. In the present invention, all of the foregoing essential components can be assembled together in the reaction mixture at room temperature, along with an effective amount of a SSB(s) as hereinafter described, yet nonspecific primer extension products are inhibited or prevented from occurring at nonstringent temperatures such as room temperature. Of course, other components which are known or conventional in the art also can be included in the reaction mixture to achieve various known or conventional effects, e.g., glycerol, betaine, DMSO, detergents, etc., the selection and incorporation of which are within the ability of one having ordinary skill in the art.

Once the PCR mixture has been prepared (all reaction components introduced into the reaction tubes in the appropriate concentrations), the tubes can be transferred to a thermal cycler to carry out the cyclic reactions for automated PCR. Less preferably, manual PCR can be used. A preferred PCR temperature profile contemplated herein is disclosed in Table 1.

The steps (and resulting products) described in Table 1 will be familiar to those having ordinary skill in the art, so they are only briefly described here. As will be understood, the Initial Denaturation step is carried out to heat-denature double-stranded template strands, and is not repeated as a part of the cycle. The cycle which is repeated many times consists of the following steps. During the Denaturation step, which is conventionally shorter in duration than the Initial Denaturation step, dsDNA is heat-denatured to generate ssDNA which can be annealed in the subsequent step. During the Hybridization step, the primer and template strands are annealed at a stringent temperature so as to produce, preferentially, a specific hybridization product, as compared to a nonspecific hybridization product which would result if hybridization were carried out at a lower, nonstringent temperature. Next, during the Extension step, a primer extension reaction is carried out at a temperature that preferably has been optimized for the particular enzyme or enzymes being used to catalyze the primer extension reaction. The foregoing cycle of steps is repeated many times (e.g. 25-45 times) to generate an amplified double-stranded primer extension product.

In the variation of PCR known as reverse-transcription PCR (RT-PCR), an additional step is carried out before the Initial Denaturation step to convert the RNA substrate to DNA by the action of a RNA-dependent, DNA polymerase (reverse transcriptase). This enzymatic conversion can be accomplished by a thermostable polymerase other than Taq DNA Polymerase (e.g., Tth DNA Polymerase) or more commonly by less thermostable polymerases such as MMLV-RT or AMV-RT. This step typically requires temperatures from 37-75° C. and times from 1-60 minutes. Following this initial template conversion step, the reactions proceed as outlined above.

The times and temperatures disclosed for the steps in Table 1 are not mandatory and are intended merely as a useful guide to select appropriate conditions. Selection of appropriate cycle step times and temperatures is well within the ability of a person having ordinary skill in the art depending on the particular nucleic acid to be amplified, the polymerase to be used, as well as other reaction-specific factors. Several of the steps in Table 1 may be omitted depending on factors well recognized by those having ordinary skill in the art. Others can be optimized for time or temperature depending on reaction-specific factors such as those mentioned above.

TABLE 1

Steps for the Polymerase Chain Reaction

| Step No. | Step Name | Temperature | Time | Effect |
|---|---|---|---|---|
| 1 | Initial Denaturation | 92-95° C. | 0.5-5 minutes | Denature double-stranded DNA template. |
| 2 | Denaturation | 92-95° C. | 1-60 seconds | Denature dsDNA. |
| 3 | Hybridization | 50-72° C. | 1-60 seconds | Primers bind to complementary target portions of template nucleic acid strands. |
| 4 | Extension | 68-72° C. | can vary, generally about 0.5-20 minutes | Polymerase extends primer thereby synthesizing new strand complementary to template strand to form dsDNA. |

Repeat steps 2-4 as necessary, generally 25-45 times to amplify template nucleic acid.

| | | | | |
|---|---|---|---|---|
| 5 | Final Extension | 68-72° C. | 5-10 minutes | Ensure full-length primer extension products. |
| 6 | Final Soak | 4-10° C. | as necessary | Storing of reaction products until needed. |

For example, the Final Extension step often is omitted. Also, the optimal temperature for Taq DNA Polymerase (and other thermostable polymerases) during the Extension step generally is between about 68-74° C. It is noted further that the Hybridization and Extension steps in Table 1 can be performed at the same temperature, simultaneously; alternatively the Extension step can be performed at a higher temperature than the Hybridization step. It is seen in Table 1 that the Extension step preferably is carried out within the temperature range of 68-72° C. However, this step can be carried out substantially in the same range of temperature as the Hybridization step; that is from 50° C. to about 72° C. depending on reaction-specific factors, particularly the polymerase or other enzyme that is used to facilitate the synthesis (primer extension) reaction during the Extension step. Alternatively, the Hybridization and Extension steps can be carried out at a temperature lower than 50° C. so long as such lower temperature is sufficiently stringent to produce hybridization, and consequent extended, products of desired specificity.

The following further points are noted for completeness:
1) Denaturation temperatures typically are less than 100° C. but greater than 90° C.; incubation time may be 1 second up to about 15 minutes. These temperatures and times are chosen to sufficiently denature dsDNA to produce ssDNA.
2) Hybridization temperatures typically are about or less than 72° C. but greater than 50° C., with the specific temperature selected depending on the melting temperature ($T_m$) of the primer(s) to provide high stringency.

Herein, a single-stranded nucleic acid binding protein (SSB) is incorporated into a primer extension reaction mixture at a low temperature (such as room temperature) that is nonstringent as to the generation of nonspecific primer extension products. The effect is that despite the presence in the reaction mixture, at low temperature, of all the necessary components for successful hybridization and primer extension reactions, the formation of specific primer extension products nonetheless is improved compared to nonspecific products. This effect is believed to result from the SSB binding to single-stranded nucleic acids in the reaction mixture at low, nonstringent temperatures that are more permissive for nonspecific primer extension products. Specifically, the SSB in effect sequesters the primers (which are single-stranded nucleic acids) in the reaction mixture at low, nonstringent temperatures at which these reaction mixtures typically are prepared.

It is believed the incorporation of SSB(s) into the primer extension reaction mixture at nonstringent temperatures may prevent or inhibit two different events. First, SSBs may prevent or inhibit primers from hybridizing to other single-stranded nucleic acids due to their binding to the primers to form an SSB-primer complex at low, nonstringent temperatures. Second, if a primer-template hybrid were to be formed, SSBs may prevent primer extension by blocking access of the polymerase to the primer strand's 3'-end, e.g., if SSB remains bound at least to the hybridized primer's 3'-end. This would inhibit the polymerase's ability to assemble nucleotides to that strand for carrying out the extension reaction.

It is noted the invention is not to be limited to either of the foregoing mechanisms, which are believed, but not certain, to be responsible in whole or in part for the observed behavior. Indeed, there may be alternative explanations as to the mechanism for the reduced generation of nonspecific primer extension products. What is evident is that the SSB(s) interacts with the primer(s) at nonstringent temperatures in some manner (e.g., through binding) so that the primers thereby are prevented, or at least inhibited, from participating in primer extension reactions at those temperatures. It further has been shown that such inhibitive interaction between SSB and the primers can be reversed through heating to an elevated temperature that is more stringent for primer-template hybridization as described more fully herein.

The present methods are referred to by the inventors as 'primer sequestration' because the primers are believed to be (or at least the effect is as though they are) sequestered, and thus prevented or inhibited from participating in primer extension reactions at nonstringent temperatures. Following preparation of the primer extension reaction mixture including all the necessary components including the SSB at low temperature, the temperature of the mixture is elevated in accordance with the amplification reaction cycle profile, e.g., as described in Table 1, to perform a desired amplification reaction. The SSB is selected such that at the temperature at which the reactions are to proceed (Hybridization and Extension steps in Table 1), the SSB is or becomes denatured, or otherwise ceases to interact with or becomes dissociated from the primers, as by breaking or disrupting a chemical or physical bond therebetween, thereby releasing the primers so they are free to participate in the reaction. Moreover, such temperatures (50-72° C. from Table 1) are stringent compared to the temperature at which the reactions were assembled, so specific annealing is thermodynamically favored over non-specific annealing.

In one embodiment, SSBs are selected which are effective to interact or associate with the primers via a thermolabile (i.e., heat-sensitive) interaction. This interaction is spontaneously disrupted at elevated temperatures, preferably at or near the range of more stringent yet optimal temperatures for polymerase activity (typically 50-75° C., more preferably 68-72° C.), but preferably not less than 30, preferably 37, preferably 40, preferably 50, degrees Celsius. In a preferred embodiment, the bond between the SSB and the single-stranded nucleic acid is a non-covalent bond that is sensitive to heating (i.e., above about 30° C., 40° C. or 50° C.). When the temperature of the reaction mixture is elevated above these temperatures, temperatures which favor specific priming, the thermolabile interaction is terminated and the primers may participate in the hybridization and subsequent extension reactions.

Alternatively, the SSBs may bind to and thereby sequester the primer molecules at a temperature at or below 30° C., but become denatured at an elevated temperature in the range of 30° C. to 98° C. or 50° C. to 98° C. (more preferably up to 96° C., more preferably up to 95° C.) such that the interaction between the primer and the SSB is terminated or caused to be terminated as a result of or in conjunction with the denaturation of the SSB, thereby releasing the associated primers such that they are free to anneal to their intended targets. In this manner, the primers are sequestered at lower, nonstringent temperatures where hybridization specificity is relatively low, but are free to form hybrids at elevated temperatures where stringency and consequently hybridization specificity are relatively high.

It is envisioned that any SSB or combination of SSBs may be useful in the present invention with the preferred (but not limited to) characteristics: 1) the SSB(s) binds primers at lower temperatures commonly used during assembly of PCR reactions (i.e., at, near or lower than room temperature, or between 0-30° C., more typically between 15-27° C.); 2) the SSB(s) binds primers in commonly used or conventional PCR buffers; and 3) the SSB(s) does not bind primers at more stringent temperatures for specific hybridization (preferably at about or greater than 30, 40, 50, 60, 70, 80, or 90, degrees Celsius). Termination of the interaction between the SSB(s)

and the primers at elevated temperatures may be due to a thermolabile bond or otherwise via denaturation of the SSB(s). This makes the primers available during the operative steps of a PCR and viable to be extended by the polymerase or polymerases in the reaction mixture.

In a preferred embodiment, the SSB used in the disclosed methods is wild-type T7 SSB, a mutant variant of T7 SSB, or a combination thereof. Wild-type T7 SSB is also known as T7 gp2.5 or T7 gene 2.5 in the scientific literature, a term that describes its coding sequence's position in the bacteriophage T7 genome. The term 'wild-type' herein means the non-mutated or original DNA and protein sequence provided in publicly available databases and literature (e.g., Dunn and Studier, 1983, *Journal of Molecular Biology* 166(4):477-535). T7 SSB forms stable dimers in solution which are composed of two identical subunits that have a molecular weight 25,562 gm mol$^{-1}$ each. T7 SSB binds with high affinity to ssDNA over dsDNA and each protein monomer binds a length of about 7 nucleotides. The thermostability of T7 SSB has been determined and its melting temperature ($T_m$) is about 53° C. The melting temperature of a protein is analogous to the melting temperature of dsDNA and is defined as the transition temperature at which about 50% of the protein is completely denatured relative to its native state. Herein, an SSB is termed 'denatured' when it is or ceases to be effective to prevent or inhibit the generation of primer extension products according to the disclosed methods, for example because it has lost its ability to bind to single-stranded nucleic acids as by heating to unwind the protein from its native or effective conformation. A thorough characterization of T7 SSB is found in Kim et al., 1992, *Journal of Biological Chemistry* 267(21):15022-15031.

SSBs are known to bind to single-stranded nucleic acids stoichiometrically. In order to produce the inhibitive effect at nonstringent temperatures as described herein, it is preferred the SSB concentration provided in a reaction mixture be sufficient to produce a stoichiometric excess of SSB relative to the primers in the mixture. Determination of the stoichiometric ratio between a particular SSB and a particular primer (or primers) is well within the ability of one having ordinary skill in the art without undue experimentation, and in fact the stoichiometric ratios for numerous SSBs are known from the published literature. In addition, most single-stranded DNA binding proteins, including the wild-type and mutant T7 SSBs discussed herein, have a binding affinity for ssDNA that is generally a few orders of magnitude greater than their affinity for dsDNA or RNA (e.g., Chase and Williams, 1986, Annual Reviews of Biochemistry 55:103-136; Lindberg et al., 1989, *Journal of Biological Chemistry* 264(21):12700-12708; Curth et al., 1996, *Nucleic Acids Research* 24(14): 2706-2711). Thus, in calculations and Examples that follow, dsDNA and/or RNA template amounts in the reaction are not taken into consideration. This approximation applies to most standard PCR reactions since generally dsDNA is the preferred or most common template.

As an example, T7 SSB (wild-type and mutant varieties) interacts with about 7 single-stranded nucleotide bases of DNA per protein molecule (also referred to as monomer). For a primer having a length of 21 nucleotide bases, this equates to a stoichiometric ratio of 3 monomers of T7 SSB per molecule of primer. Depending on the concentration of the primer and the molecular weight of the protein, an appropriate concentration for the SSB can be determined through simple arithmetic to produce a desired stoichiometric excess of SSBs. As evidenced in Example 4 below, it is desirable to have at least a 50 percent stoichiometric excess of SSBs versus primers in the reaction mixture, or a stoichiometric ratio of 1.5. Even more preferred is a 100 percent stoichiometric excess (a 1-fold excess, stoichiometric ratio of 2). Still more preferred is a 2-fold, 3-fold, or 4-fold excess of SSBs versus primers, corresponding to stoichiometric ratios of 3, 4 and 5, respectively.

For the primer sequestration methods disclosed herein, the wild-type or naturally occurring T7 SSB is preferred. For convenience, the amino acid sequence of wild-type T7 SSB is provided in the Sequence Listing as SEQ ID NO. 4; the DNA gene sequence that codes for wild-type T7 SSB also is provided as SEQ ID NO. 3. In addition to the wild-type protein, the mutants T7 gp2.5 Δ21C (SEQ ID NO. 5), T7 gp2.5 F232L (SEQ ID NO. 7) and a mixture of wild-type and T7 gp2.5 Δ26C (SEQ ID NO. 6) also have proven useful as will be shown in the following Examples, and also are preferred. T7 SSB mutants Δ21C (SEQ ID NO. 5) and Δ26C (SEQ ID NO. 6) have a deletion of the last 21 and 26 amino acids of the wild-type protein, respectively. They have been shown to bind single-stranded DNA with at least 10-fold greater affinity over the wild-type protein (e.g., T. Hollis et al., 2001, *Proceedings of the National Academy of Sciences* 98(17):9557-9562; Rezende et al., 2002, *Journal of Biological Chemistry* 277(52):50643-50653; Hyland et al., 2003, *Journal of Biological Chemistry* 278(9):7247-7256; He et al., 2003, *Journal of Biological Chemistry* 278(32):29538-29545). T7 SSB mutant F232L (SEQ ID NO. 7) is a change of the 232$^{nd}$ amino acid of the protein from phenylalanine to leucine and has been previously shown to bind single-stranded DNA with about 3-fold greater affinity than the wild-type protein (He et al., 2003, *Journal of Biological Chemistry* 278(32):29538-29545). It is noted that other mutants of T7 SSB not listed herein also may be useful in the disclosed methods.

In less preferred embodiments, certain mutant *E. coli* SSBs and T4 SSB (both wild-type and mutant varieties) also may be useful to provide a sufficient primer sequestration effect at nonstringent temperatures as described herein, e.g., through reversible interaction (such as binding) with the primers at those temperatures. It is noted that wild-type *E. coli* SSB has been found to be unsuitable for use in the disclosed methods because it has been shown to interfere with PCR (see Example 1). When wild-type *E. coli* SSB is used in stoichiometric excess over the primers, PCR amplification products are not observed. Thus, this SSB appears to continue to bind or interact with the primers even at the elevated, more stringent temperatures required for specific primer-template hybridization. A potential explanation is that it is well-known *E. coli* SSB retains some binding activity even after boiling for up two minutes (Chase and Williams, 1986, *Annual Reviews of Biochemistry* 55:103-136). Thus, unlike T7 SSB, wild-type *E. coli* SSB appears to be able to withstand exposure to high temperatures and its inhibitive effects on primer extension reactions are not readily thermally inactivated.

Other SSBs not particularly described herein are suitable for use in the present invention so long as they meet the criteria outlined previously.

The inventors have cloned the nucleotide sequence for, and expressed and purified protein from, wild-type and mutant forms of T7 SSB as described below. The following procedures are well within reasonable standards for those of ordinary skill in the art. The growth and purification procedures can be modified from those described below depending on the binding protein being purified as well as contaminants present in the preparation.

Preparation of Wild-Type and Mutant Variety T7 SSBs

Construction of T7 SSB expression plasmid—Two primers, δ 5'-end primer with a Nde restriction site (5'-ATC-CAT- ATG-GCT-AAG-AAG-ATT-TTC-ACC-TCT-GCG-3', SEQ ID NO. 1) and a 3' end primer with SalI and XmaI restriction sites (5'-GTC-GAC-CCC-GGG-TTA-GAA-GTC-GCC-GTC-TTC-GTC-TGC-TTC-C-3', SEQ ID NO. 2) were used to PCR-amplify the wild-type T7 SSB gene nucleotide sequence from positions 9158-9856 in purified bacteriophage T7 genomic DNA (USB Corporation, Cleveland, Ohio). The complete genome sequence for T7 can be found at locus NC_001604 at the National Center for Biotechnology Information (NCBI). Bacteriophage T7 is publicly available from the American Type Culture Collection (ATCC) under catalog numbers 11303-B38™ and BAA-1025-B2™. The sequences for wild-type T7 gene 2.5, its corresponding protein (wt T7 gp2.5, also referred to as T7 SSB) and the mutant varieties thereof which are discussed herein are provided in the Sequence Listing for convenience and ease of reference.

PCR generated DNA fragments (wild-type T7 SSB gene) were ligated into TOPOII™ vector (Invitrogen Corporation), transformed into TOP 10™ chemically competent E. coli (Invitrogen Corporation) and the resulting plasmid containing the wild-type T7 SSB gene (SEQ ID NO. 3) was selected in presence of kanamycin. The clone generated from PCR-amplified DNA was sequenced and found to be free of mutations. The plasmid was then cut with NdeI and XmaI and cloned into the pRE expression vector. This expression vector is under the control of the powerful promoter pL from the bacteriophage λ which is repressed by the λ repressor at 30° C. The expression from the pL containing vector is induced by raising the temperature to 42° C. The resulting plasmid containing T7 SSB (SEQ ID NO. 4) was selected in presence of ampicillin. All mutant forms of T7 SSB prepared herein were expressed from the base DNA clones described in this paragraph, which were first altered using reverse primers that either incorporated base changes to alter amino acids or introduced a stop codon to terminate protein synthesis at the desired location depending on the mutation to be prepared.

Growth and purification of T7 SSB—The plasmid pRE containing the wild-type or mutant varieties of T7 SSB prepared herein, under the control of λ promoter, was grown overnight at 30° C. in 500 ml Terrific Broth and 100 μg/ml ampicillin. This culture was used to inoculate 10 liters of TB and 50 μg/ml ampicillin in a New Brunswick fermentor. The cells were incubated with aeration at 30° C. At a cell density corresponding to $A_{590}$=1.53, the cells were induced by raising the temperature to 42° C. to induce the expression of T7 SSB. After induction, the cells were incubated for 2 additional hours and then harvested by centrifugation at 6,000 rpm for 15 minutes in a Sorvall GS-3 rotor. The cell paste (83 gm) was then stored at −80° C.

Preparation of cell extract—20 gm of frozen cells were thawed in 80 ml of 50 mM Tris-HCl (pH 7.5), 1 mM EDTA, 10% sucrose, 100 mM NaCl, 2 mM PMSF and 10 ml of lysozyme (10 mg/ml) were added. After incubation of the mixture for 30 minutes on ice with constant stirring, 21 ml of 5M NaCl were added to bring the final concentration of NaCl to 1 M. The cells were then heated in a 37° C. water bath with constant stirring until the temperature reached 20° C. and then cooled in an ice water bath until the temperature was reduced to 4° C. The lysate was then centrifuged for 45 minutes at 40,000 rpm in a Beckman Ti-45 rotor. The supernatant (122 ml) was Fraction I.

DEAE Cellulose chromatography—A column of Whatman DE52 DEAE cellulose (19.6 $cm^2$×5 cm) was prepared and equilibrated with 50 mM Tris-HCl (pH 7.5), 1 mM EDTA, 10% glycerol (Buffer A) containing 350 mM NaCl. Fraction I was diluted with Buffer A to give a conductivity equivalent to Buffer A containing 350 mM NaCl. The diluted Fraction I (~350 ml) was applied to the column. T7 SSB is not retained under these conditions. The flow through and wash fractions (~400 ml) were pooled to give fraction II.

Ammonium Sulfate Precipitation—To 400 ml of fraction II, ammonium sulfate was added to 75% saturation (203 gm) over a period of 60 minutes and was stirred slowly for an additional 60 minutes. The precipitate was collected by centrifugation at 14,000 rpm for 45 minutes in a Sorvall GSA rotor and dissolved in 50 ml of Buffer A containing 25 mM NaCl and dialyzed overnight against the same buffer (Fraction III).

Heparin Sepharose CL-6B Chromatography—A column of Heparin (0.64 $cm^2$×12 cm) was prepared and equilibrated with Buffer A containing 25 mM NaCl. Fraction III was applied to the column and eluted with a linear gradient from 25 mM to 1 M NaCl. The fractions were analyzed on SDS-PAGE and the fractions (134 ml) containing the T7 SSB were pooled and dialyzed overnight against Buffer A containing 100 mM NaCl (Fraction IV).

DEAE Sephacel Chromatography—A column of DEAE Sephacel (5.30 $cm^2$×12 cm) was prepared and equilibrated with Buffer A containing 100 mM NaCl. Fraction III was applied to the column and eluted with a linear gradient from 100 mM to 500 mM NaCl. The fractions were analyzed on SDS-PAGE. Fractions containing T7 SSB appeared to be homogeneous as a single band judged by electrophoresis under denaturing conditions, but contained a low level of single stranded DNA dependent nucleoside 5'-triphosphatase activity. The fractions (64 ml) containing the T7 SSB were pooled and dialyzed overnight against Buffer A containing 100 mM NaCl (Fraction V).

Q Sepharose Chromatography—To remove the contaminating ssDNA dependent ATPase activity, fraction V was applied to Q Sepharose and eluted with a linear gradient from 100 mM to 500 mM NaCl. The ssDNA dependent ATPase activity eluted from the column slightly before the bulk of the SSB protein. Final fractions of T7 SSB were pooled and dialyzed against 20 mM Tris-HCl (pH 7.5); 1 mM EDTA; 0.5 mM DTT; 10 mM NaCl; 50% glycerol and stored at −20° C. (Fraction VI).

Protein Concentration—The protein concentration was determined using the BCA Protein Determination Assay Kit (Pierce, Rockford, Ill.) against a BSA standard curve. After SDS-PAGE electrophoresis of the purified SSB protein under denaturing conditions, staining with Coomassie Blue produced a single band corresponding to a molecular weight of approximately 30,000. Although the molecular weight of the wild-type T7 SSB deduced from the DNA sequence of its gene is 25,562, it migrates as a single band between 25,000 and 31,000 on SDS-PAGE (this aberrant migration was also observed in Scherzinger et al., 1973, *Molecular and General Genetics* 123(3):247-262; Reuben and Gefter, 1973, *Proceedings of the National Academy of Sciences* 70(6): 1846-1850).

The inventors herein have discovered, surprisingly and unexpectedly, that T7 SSB, both wild-type and mutant varieties, prevent or inhibit primer extension reactions at lower temperatures (e.g., less than about 50° C., and particularly less than about 30° C.) but that such inhibitive effect is lost at higher, more stringent temperatures (e.g., greater than about 50° C.). Also, the inventors have discovered, surprisingly and unexpectedly, that inclusion of T7 SSB and/or its mutant forms in PCR prior to the Initial Denaturation step leads to less amplification artifacts. This unexpected result is believed to occur because nonspecific priming events and/or primer extension products are not formed or are inhibited from being formed at the lower temperatures at which PCR mixtures typically are assembled or prepared. Thus, the primers are sequestered at temperatures where specificity tends to be low before the reaction mixture is heated, and then the primers are released and thus available for hybridization and polymerization at higher, more stringent temperatures. In this manner, it has been observed that amplification of unintended targets formed due to low hybridization specificity (at low temperature) has been substantially reduced.

The following Examples illustrate the effectiveness of a variety of T7 SSBs in preventing or inhibiting the generation of nonspecific primer extension products, and are presented by way of illustration and not limitation.

EXAMPLE 1

A 306 base pair (bp) region of the gene product Numb (sequence provided at SEQ ID NO. 8) was amplified, separately, under a variety of different conditions of SSB species and concentration, selection of polymerase, etc., as further described below, from 5 nanograms (ng) of human genomic DNA. The target is identified as NT_026437.11 at NCBI (sequence location: 54742877 to 54743182). The following amplification primers were used, each of which was 25 bases in length;

```
Numb Forward:
5'-GAGGTTCCTACAGGCACCTGCCCAG-3'    (SEQ ID NO. 9)

and

Numb Reverse:
5'-CAAAATCACCCCTCACAGTACTCTG-3'.   (SEQ ID NO. 10)
```

Primers were from standard commercial suppliers and resuspended in TE (10 mM Tris-HCl (pH 8), 1 mM EDTA) at desired concentrations. Human genomic DNA was from Promega Corporation, Madison, Wis. These primers were chosen because they have several bases of complementary sequence at the 3'-end between the forward and reverse primers and generate nonspecific amplification products.

A total of 15 polymerase chain reaction mixtures were assembled at room temperature (i.e., 20-25° C.) in 0.5 milliliter (ml) microfuge tubes with the following general components listed in Table 2 in a final volume of 25 microliters (µl):

TABLE 2

| Components | Volume for 25 µl reaction | Final Concentration |
| --- | --- | --- |
| Water | 19.875 µl | NA |
| 10× PCR Buffer | 2.5 µl | 1× |
| 5 mM dNTP Mixture | 1.0 µl | 0.2 mM each dNTP |
| 10 µM Forward and Reverse Primers | 0.5 µl | 0.2 µM or 5 pmol each/reaction |
| Template DNA | 0.5 µl | 5 ng/reaction |
| SSB, 2 mg/ml | 0.5 µl | 1 µg/reaction |
| Taq DNA Polymerase, 5 U/µl | 0.125 µl | 0.625 units/reaction |

The 15 PCR reaction mixtures had the following specific attributes:

Reaction 1: antibody-bound Taq DNA Polymerase, no SSB;
Reaction 2: chemically-modified Taq DNA Polymerase, no SSB;
Reaction 3: unmodified Taq DNA Polymerase, no SSB;
Reaction 4: 1 µg wild-type *E. coli* SSB, antibody-bound Taq DNA Polymerase
Reaction 5: 1 µg wild-type *E. coli* SSB, chemically-modified Taq DNA Polymerase;
Reaction 6: 1 µg wild-type *E. coli* SSB, unmodified Taq DNA Polymerase;
Reaction 7: 1 µg wild-type T7 SSB, antibody-bound Taq DNA Polymerase;
Reaction 8: 1 µg wild-type T7 SSB, chemically-modified Taq DNA Polymerase;
Reaction 9: 1 µg wild-type T7 SSB, unmodified Taq DNA Polymerase;
Reaction 10: 1 µg Δ21C T7 SSB, antibody-bound Taq DNA Polymerase;
Reaction 11: 1 µg Δ21C T7 SSB, chemically-modified Taq DNA Polymerase;
Reaction 12: 1 µg Δ21C T7 SSB, unmodified Taq DNA Polymerase;
Reaction 13: 1 µg F232L T7 SSB, antibody-bound Taq DNA Polymerase;
Reaction 14: 1 µg F232L T7 SSB, chemically-modified Taq DNA Polymerase;
Reaction 15: 1 µg F232L T7 SSB, unmodified Taq DNA Polymerase.

To minimize pipetting errors, two separate master mixes were assembled. Master Mix 1 was a 6× mix that contained water, PCR buffer, dNTPs, and the respective polymerase. Master Mix 2 was a 20× mix that contained the human genomic DNA and primers. The components were added in the following order to the reaction tubes at room temperature; 23.5 µl of the appropriate Master Mix 1 (i.e., with respective polymerase), 0.5 µl of the SSB or SSB Storage Buffer when performing controls, and 1 µl of Master Mix 2. It is noted that the concentration of T7 gp2.5 Δ21C used in Reactions 10-12 was 0.5 mg/ml, not 2 mg/ml as in the other reaction mixtures, and thus 2 µl of this protein were added per 25 µl reaction instead of 0.5 µl to achieve the same total SSB concentration for Reactions 10-12.

The 10×PCR buffer consisted of 100 mM Tris-HCl (pH 8.6), 500 mM KCl, and 15 mM $MgCl_2$. The 5 mM dNTP mixture contained the four deoxyribonucleotides required for DNA synthesis (dATP, dGTP, dTTP, and dCTP). The SSBs from T7 were prepared as described elsewhere herein. *E. coli* SSB and unmodified Taq DNA Polymerase (i.e., non-hot-start) were from USB Corporation, Cleveland, Ohio. SSBs were added to the respective reaction mixtures before the primers and template. For control reactions without SSBs, the SSB storage buffer, without SSBs, was added instead. For comparison, two commercially available hot-start products were used in place of standard (unmodified) Taq DNA Polymerase, Reactions 1, 4, 7, 10, and 13 and 2, 5, 8, 11, and 14, respectively. The antibody-bound Taq DNA Polymerase (tradename Platinum™ Taq DNA Polymerase) used in Reactions 1, 4, 7, 10, and 13 was from Invitrogen Corporation, Carlsbad, Calif. The chemically-modified Taq DNA Polymerase (tradename HotStarTaq™ DNA Polymerase) used in Reactions 2, 5, 8, 11, and 14 was from Qiagen Incorporated, Valencia, Calif.

After all the reaction mixtures were completely assembled, they were incubated at room temperature (i.e., 20-25° C.) for a period of 30 minutes before the reactions tubes were placed in the thermal cycler. This extra time at room temperature was chosen so as to favor the generation of nonspecific products. Following this room temperature incubation, reactions tubes were placed in a thermal cycler (MJ Research, Waltham, Mass.) with the following cycling conditions shown in Table 3 common among all the reactions except as otherwise noted:

TABLE 3

| Step | Temperature | Time |
|---|---|---|
| Initial Denaturation | 95° C. | 2 minutes or 15 minutes |
| Denaturation | 95° C. | 10 seconds |
| Hybridization | 63° C. | 30 seconds |
| Extension | 72° C. | 30 seconds |
| Repeat previous three steps 35 times | | |
| Final Extension | 72° C. | 5 minutes |
| Final Soak | 10° C. | as necessary |

It is noted that the Initial Denaturation time was 2 minutes for reactions containing the unmodified Taq DNA polymerase and the antibody-bound Taq DNA polymerase, and 15 minutes for the chemically-modified Taq DNA polymerase as per the manufacturer's instructions.

Following cycling, 10 µl from each of the polymerase chain reactions were electrophoresed on a 2% TAE agarose gel containing ethidium bromide run at 100-120 volts for about 1-2 hours in 1×TAE buffer. The primer extension reaction products were visualized using a fluorescent scanner (Hitachi FMBIO II, San Francisco, Calif.).

The results of the foregoing reactions are shown in FIG. 1, wherein the numbered lanes correspond to the like-numbered Reactions described above and the Marker Lane, M, was provided using 1 Kb Plus DNA Ladder from Invitrogen Corporation, Carlsbad, Calif.

As seen in FIG. 1, the presence of wild-type T7 SSB, as well as the T7 SSB mutants referred to herein as Δ21C and F232L markedly improved the yield of specific primer extension products compared to standard Taq DNA Polymerase which does not have a hot-start feature (compares lane 3 to lanes 9, 12, and 15). In the control reaction without SSB (lane 3), primer-dimers are primarily generated at the expense of the specific product of 306 bp. Thus, the SSBs reduced or eliminated these nonspecific primer-dimers and allowed the generation of the specific product. In addition, this enhancement effect was shown to be comparable, if not equal, to the two commercially available hot-start polymerases used in this experiment (compare lanes 1, 2 to lanes 9, 12, and 15). There appeared to be no general effect of adding SSBs into reactions using polymerases which already included a built-in hot-start feature (compare lane 1 to lanes 7, 10, and 13 as well as lane 2 to lanes 8, 11, and 14). It is noted that wild-type *E. coli* SSB (lanes 4-6) completely inhibited the formation of any primer extension products. Thus, wild-type *E. coli* SSB is unsuitable for use in the present methods as it inhibits the generation of amplified extension products through PCR. This experiment demonstrated the effectiveness of not only wild-type T7 SSB, but also mutant varieties of T7 SSB in which specific amino acids have been changed or deleted.

EXAMPLE 2

This example illustrates the effectiveness of a mixture of wild-type and mutant T7 SSB in the hot-start method. Specifically, this example uses a 1:1 mass ratio of wild-type T7 SSB to Δ26C protein in a polymerase chain reaction to reduce the generation of nonspecific primer extension products. In this experiment, 1 microgram (µg) of the mixture contained 0.5 µg of each protein. An 1142 base pair (bp) region of the gene product p53 (SEQ ID NO. 11) was amplified from either 1 nanogram (ng) or 100 picograms (pg) of human genomic DNA. This target is identified as NT_010718.15 at NCBI (sequence location: 7174821 to 7175962). The following amplification primers were used;

p53 Forward:
5'-TGCTTTATCTGTTCACTTGTGCCC-3' (SEQ ID NO. 12)
24 bases in length, and p53 Reverse:
5'-TGTGCAGGGTGGCAAGTGGC-3' (SEQ ID NO. 13)
20 bases in length.

Primers were from standard commercial suppliers and resuspended in TE (10 mM Tris-HCl (pH 8), 1 mM EDTA) at desired concentrations. Human genomic DNA was from Promega Corporation, Madison, Wis. These primers were chosen because they have several bases of complementary sequence at the 3'-end between the forward and reverse primers and generate nonspecific amplification products.

A total of 8 polymerase chain reaction mixtures were assembled at room temperature (i.e., 20-25° C.) in 0.5 milliliter (ml) microfuge tubes with the following general components as shown in Table 4 in a final volume of 25 microliters (µl):

TABLE 4

| Components | Volume for 25 µl reaction | Final Concentration |
|---|---|---|
| Water | 20.175 µl | NA |
| 10× PCR Buffer | 2.5 µl | 1× |
| 25 mM dNTP Mixture | 0.2 µl | 0.2 mM each dNTP |
| 10 µM Forward and Reverse Primers | 0.5 µl | 0.2 µM or 5 pmol each/reaction |
| Template DNA | 1.0 µl | variable |
| SSB | 0.5 µl | variable |
| Taq DNA Polymerase, 5 U/µl | 0.125 µl | 0.625 units/reaction |

The 8 PCR reaction mixtures had the following specific attributes:
Reaction 1: 100 pg genomic DNA, no SSB;
Reaction 2: 0.5 µg T7 SSB mix, 100 pg genomic DNA;
Reaction 3: 1.0 µg T7 SSB mix, 100 pg genomic DNA;
Reaction 4: 2.0 µg T7 SSB mix, 100 pg genomic DNA;
Reaction 5: 1 ng genomic DNA, no SSB;
Reaction 6: 0.5 µg T7 SSB mix, 1 ng genomic DNA;
Reaction 7: 1.0 µg T7 SSB mix, 1 ng genomic DNA;
Reaction 8: 2.0 µg T7 SSB mix, 1 ng genomic DNA.

To minimize pipetting errors, three separate master mixes were assembled. Master Mix 1 was a 10× mix that contained water, PCR buffer, dNTPs, and Taq DNA Polymerase. Master Mix 2 was a 10× mix that contained water, 100 pg/reaction human genomic DNA, and primers. Master Mix 3 was a 10× mix that contained water, 1 ng/reaction human genomic DNA, and primers. It is noted that the final water volume from Table 4 was divided such that 48% of the final volume was present in mix 1 and 52% of the final volume was present in mix 2 or mix 3. The components were added in the following order to the reaction tubes at room temperature; 12.5 µl of Master Mix 1, 0.5 µl of the SSB, or SSB Storage Buffer when performing controls, and 12 µl of Master Mix 2 or Master Mix 3 as appropriate.

The 10×PCR buffer consisted of 100 mM Tris-HCl (pH 8.6), 500 mM KCl, and 15 mM $MgCl_2$. The 25 mM dNTP mixture contained the four deoxyribonucleotides that are required for DNA synthesis (dATP, dGTP, dTTP, and dCTP). The SSBs from T7 were prepared as described elsewhere herein except the final storage buffer was changed to 20 mM Tris-HCl (pH 8.5), 200 mM KCl, 1 mM DTT, 0.1 mM EDTA, 0.5% Tween-20, and 50% glycerol. Serial dilutions of the SSB mixture were performed in final storage buffer in order to add 0.5 µl per reaction. For control reactions without SSB, the SSB storage buffer, without any SSBs, was added instead. SSB was added to the reaction mixture before the primers and template. Serial dilutions of the human genomic DNA were performed in nuclease-free water. Taq DNA Polymerase was from USB Corporation, Cleveland, Ohio.

After the reaction mixtures were completely assembled, the reaction tubes were placed in a thermal cycler (MJ Research, Waltham, Mass.) using the cycling conditions as listed below in Table 5. It is noted that an additional pre-incubation step at 25° C. for one hour was programmed into the thermal cycler so as to simulate room temperature. This extra time at 25° C. was chosen so as to favor the generation of nonspecific products.

TABLE 5

| Step | Temperature | Time |
|---|---|---|
| Initial Soak | 25° C. | 60 minutes |
| Initial Denaturation | 95° C. | 2 minutes |
| Denaturation | 95° C. | 10 seconds |
| Hybridization | 60° C. | 5 seconds |
| Extension | 72° C. | 2 minutes |
| Repeat previous three steps 35 times | | |
| Final Extension | 72° C. | 5 minutes |
| Final Soak | 10° C. | as necessary |

Following cycling, 10 µl from each of the polymerase chain reactions were electrophoresed on a 1.5% TAE agarose gel containing ethidium bromide run at 100-120 volts for about 1-2 hours in 1×TAE buffer. The primer extension reaction products were visualized using a fluorescent scanner (Hitachi FMBIO II, San Francisco, Calif.).

The results of the foregoing reactions are shown in FIG. 2, wherein the numbered lanes correspond to the like-numbered Reactions described above, and the Marker Lanes, M, were provided using 1 Kb Plus DNA Ladder from Invitrogen Corporation, Carlsbad, Calif.

As seen in FIG. 2, the presence of 1:1 mass ratio mixture of wild-type T7 SSB to its mutant Δ26C markedly improved the yield of specific primer extension products compared to the control lanes in which no SSB was introduced (compare lane 1 to lanes 2, 3, and 4 as well as lane 5 to lanes 6, 7, and 8). The specific product was an 1142 bp fragment of the p53 gene and is indicated by the upper arrow in FIG. 2. At the lower concentration of DNA (100 pg), the control reaction (lane 1) did not produce appreciable specific product but instead primarily produced nonspecific product characterized as primer-dimers. At 1 ng of human genomic DNA, the control reaction did produce some specific product, but also produced some primer-dimers. The reactions in which the SSB mixture was present all produced more specific product and reduced or eliminated nonspecific products. One can observe that there is a concentration dependent effect in which increasing concentrations of SSB (from 0.5 µg to 2 µg) yielded increasing amounts of specific product (e.g., compare lanes 2, 3, and 4). This was believed due to the stoichiometry of SSB binding to the primers in the reaction. This effect will be elaborated on in a later example.

EXAMPLE 3

This example further illustrates the effectiveness of mixtures of wild-type and mutant T7 SSB in blocking primer extension at room temperature. Specifically, this example uses a 1:1 mass ratio of wild-type T7 SSB to Δ26C protein in a 'mock' polymerase chain reaction in which primer extension was directed at two primers that were purposefully designed to form hybrids. Thus, there was no exogenous dsDNA template in the reaction, only the primers themselves serve as template for synthesis. This assay was designed to access the ability of SSB to block DNA synthesis from an extendable hybrid at two temperatures. The first temperature was room temperature (25° C.), as this simulated the temperature at which reactions are generally assembled. The second was at 72° C., which is a more optimal temperature for DNA synthesis by Taq DNA Polymerase.

Figure 3A:
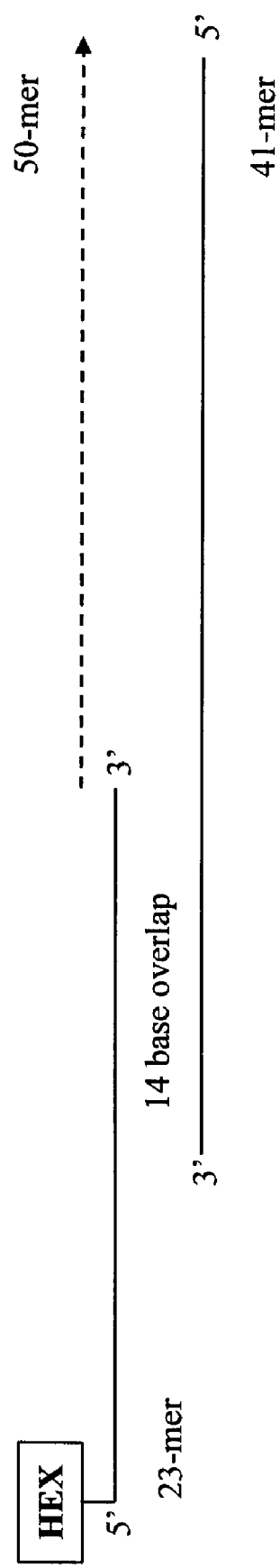
FIG. 3a is a schematic of the polymerase blocking assay of Example 3. The forward primer has a HEX label attached to its 5' end to allow fluorescent detection. The primer extension product is a 27 base addition to the 23-base forward primer. The observed change during denaturing PAGE is from 23 to 50 bases.

The two primers chosen for this experiment were designed to form a dsDNA hybrid with 14 bp of overlap at their 3'-ends. The forward primer of 23 bases had a HEX fluorescent label attached to its 5' end which enabled detection of the synthesis product on a fluorescent scanner. Since the reverse primer of 41 bases has 14 bp of overlap with the forward primer, the maximum synthesis product that could be generated from the forward primer was 50 bases. This primer extension product was visualized during denaturing polyacrylamide gel electrophoresis. A schematic of the assay is shown in FIG. 3a.

In this assay, 1 pmol of each primer was placed in a 10 µl reaction volume and tested against several concentrations of the SSB mixture. The primer sequences were as follows;

(SEQ ID NO. 14)
Forward:
5'-[HEX]-CTTTTCCCAGTCACGACGTTGTA-3'
23 bases in length, and (SEQ ID NO. 15)
Reverse:
5'-ATGCAAGCTTGGCACTGGCCGTCGTTTTACAACGTCGTGAC-3'
41 bases in length.

Primers were from standard commercial suppliers and resuspended in TE (10 mM Tris-HCl (pH 8), 1 mM EDTA) at desired concentrations. A total of 10 mock polymerase chain reaction mixtures were assembled at room temperature (i.e., 20-25° C.) in 0.5 milliliter (ml) microfuge tubes with the following general components as listed in Table 6 in a final volume of 10 microliters (µl):

TABLE 6

| Components | Volume for 10 µl reaction | Final Concentration |
|---|---|---|
| Water | 8.27 µl | NA |
| 10× PCR Buffer | 1.0 µl | 1× |
| 25 mM dNTP Mixture | 0.08 µl | 0.2 mM each dNTP |
| 10 µM Forward and Reverse Primers | 0.1 µl | 0.1 µM or 1 pmol each/reaction |
| SSB | 0.5 µl | variable |
| Taq DNA Polymerase, 5 U/µl | 0.05 µl | 0.25 units/reaction or none |

The 10 mock PCR reaction mixtures had the following specific attributes:
Reaction 1: no SSB, no Taq DNA Polymerase, 25° C. incubation;
Reaction 2: Taq DNA Polymerase, no SSB, 25° C. incubation;
Reaction 3: 0.5 µg T7 SSB mix, Taq DNA Polymerase, 25° C. incubation;

Reaction 4: 1.0 µg T7 SSB mix, Taq DNA Polymerase, 25° C. incubation;
Reaction 5: 2.0 µg T7 SSB mix, Taq DNA Polymerase, 25° C. incubation;
Reaction 6: no SSB, no Taq DNA Polymerase, 72° C. incubation;
Reaction 7: Taq DNA Polymerase, no SSB, 72° C. incubation;
Reaction 8: 0.5 µg T7 SSB mix, Taq DNA Polymerase, 72° C. incubation;
Reaction 9: 1.0 µg T7 SSB mix, Taq DNA Polymerase, 72° C. incubation;
Reaction 10: 2.0 µg T7 SSB mix, Taq DNA Polymerase, 72° C. incubation.

To minimize pipetting errors, three separate master mixes were assembled. Master Mix 1 was a 12× mix that contained water, PCR buffer, dNTPs, and Taq DNA Polymerase. Master Mix 2 was a 12× mix that contained water, PCR buffer, dNTPs, but no Taq DNA Polymerase. Master Mix 3 was a 12× mix that contained water and primers. It is noted that the final water volume from Table 6 was divided such that 46.8% of the final volume was present in mix 1 or mix 2 and 53.2% of the final volume was present in mix 3. The components were added in the following order to the reaction tubes at room temperature; 5.0 µl of Master Mix 1 or Master Mix 2 as appropriate, 0.5 µl of the SSB or SSB Storage Buffer when performing controls, and 4.5 µl of Master Mix 3.

The 10×PCR buffer consisted of 100 mM Tris-HCl (pH 8.6), 500 mM KCl, and 15 mM $MgCl_2$. The 25 mM dNTP mixture contained the four deoxyribonucleotides that are required for DNA synthesis (dATP, dGTP, dTTP, and dCTP). The SSBs from T7 were prepared as described elsewhere herein except the final storage buffer was changed to 20 mM Tris-HCl (pH 8.5), 200 mM KCl, 1 mM DTT, 0.1 mM EDTA, 0.5% Tween-20, and 50% glycerol. Serial dilutions of the SSB mixtures were performed in final storage buffer in order to add 0.5 µl per reaction. For control reactions without SSB, the SSB storage buffer, without any SSBs, was added instead. SSB was added to the reaction mixture before the primers. Negative control reactions without Taq DNA Polymerase (i.e., those that would be a baseline to judge primer extension product yields) had the balance made up with water. Taq DNA Polymerase was from USB Corporation, Cleveland, Ohio.

After the reaction mixtures were completely assembled, the reaction tubes were placed in a thermal cycler (MJ Research, Waltham, Mass.). One set of identical reactions was subjected to 25° C. for four hours to over-estimate the amount of time required to assemble PCR reactions. The other identical set was subjected to 15 cycles at 25° C. for 15 seconds and 72° C. for 15 seconds to provide ideal synthesis conditions for Taq DNA Polymerase and to determine if the SSBs were still inhibitory. Following these incubations, the reactions were stored at 4° C. or on ice until required. In order to visualize primer extension products, 0.5 µl (0.05 pmol of each primer) of each reaction were electrophoresed on a 15% (29:1) denaturing polyacrylamide gel with 42% urea. The gel was cast with 1 mm spacers in 1×GTG buffer (USB Corporation, Cleveland, Ohio) and run at a constant power of 6 watts per gel until a tracer dye (Bromo-cresol Green) had run about 75% the length of the gel (about 25 minutes). The primer extension reaction products were visualized using a fluorescent scanner (Hitachi FMBIO II, San Francisco, Calif.).

The results of the foregoing reactions are shown in FIG. 3b, wherein the numbered lanes correspond to the like-numbered Reactions described above.

As seen in FIG. 3b, following four hours of incubation at 25° C., Taq DNA Polymerase yields a primer extension product of 50 bases from the primer-hybrid compared to the negative control in which no polymerase was present in the reaction (compare lane 1 to lane 2). In addition, at the 3 concentrations of SSB tested, the presence of the 1:1 mass ratio mixture of wild-type T7 SSB to its mutant Δ26C blocked synthesis from the primer-hybrid at 25° C. comparable to the negative control (compare lanes 1 and 2 to lanes 3-5). In contrast, using a 72° C. incubation temperature yielded reaction products that were of similar yields in all of the lanes that included Taq DNA Polymerase, even when SSBs were incorporated into the reaction mixture (compare lanes 6-10). The fact that primer extension could take place at elevated, or stringent, temperatures demonstrated the blocking effect of the single-stranded binding proteins had been terminated. This experiment confirmed several desirable attributes of SSBs for use in the methods described herein: 1) interaction with ssDNA at lower temperatures at which reactions are conventionally assembled effective to inhibit the generation of extension products at those temperatures; 2) such interaction with ssDNA in conventional PCR buffers; and 3) termination of this interaction with ssDNA at more stringent temperatures.

EXAMPLE 4

This example illustrates a useful range of effective concentrations of T7 SSB that achieve the desired effect of reducing the generation of nonspecific primer extension products.

The following experiment was designed taking into account both a) the stoichiometric binding ratio of T7 SSB of 7 nucleotides bound per protein monomer, and b) the total amount of primers (ssDNA) in a given reaction. The experiment was an amplification of the Numb target of 306 bp from 1 ng of human genomic DNA that was used in Example 1. The primers were each 25 bases in length as follows:

Numb Forward:
5'-GAGGTTCCTACAGGCACCTGCCCAG-3'    (SEQ ID NO. 8)

and

Numb Reverse:
5'-CAAAATCACCCCTCACAGTACTCTG-3'.    (SEQ ID NO. 9)

Primers were from standard commercial suppliers and resuspended in TE (10 mM Tris-HCl (pH 8), 1 mM EDTA) at desired concentrations. Human genomic DNA was from Promega Corporation, Madison, Wis. Recall, these primers were chosen because they have several bases of complementary sequence at the 3'-end between the forward and reverse primers and generate nonspecific amplification products.

A total of 7 polymerase chain reaction mixtures were assembled at room temperature (i.e., 20-25° C.) in 0.5 milliliter (ml) microfuge tubes with the following general components as listed in Table 7 in a final volume of 25 microliters (µl):

TABLE 7

| Components | Volume for 25 µl reaction | Final Concentration |
| --- | --- | --- |
| Water | 20.175 µl | NA |
| 10× PCR Buffer | 2.5 µl | 1× |
| 25 mM dNTP Mixture | 0.2 µl | 0.2 mM each dNTP |

TABLE 7-continued

| Components | Volume for 25 μl reaction | Final Concentration |
| --- | --- | --- |
| 10 μM Forward and Reverse Primers | 0.5 μl | 0.2 μM or 5 pmol each/reaction |
| Template DNA | 1.0 μl | 1 ng/reaction |
| SSB | 0.5 μl | variable |
| Taq DNA Polymerase, 5 U/μl | 0.125 μl | 0.625 units/reaction |

The 7 PCR reaction mixtures had the following specific attributes:

Reaction 1: no SSB;

Reaction 2: 0.0625 μg wild-type T7 SSB;

Reaction 3: 0.125 μg wild-type T7 SSB;

Reaction 4: 0.25 μg wild-type T7 SSB;

Reaction 5: 0.5 μg wild-type T7 SSB;

Reaction 6: 1.0 μg wild-type T7 SSB;

Reaction 7: 2.0 μg wild-type T7 SSB.

To minimize pipetting errors, two separate master mixes were assembled. Master Mix 1 was a 10× mix that contained water, PCR buffer, dNTPs, and Taq DNA Polymerase. Master Mix 2 was a 10× mix that contained water, 1 ng/reaction human genomic DNA, and primers. It is noted that the final water volume from Table 7 was divided such that 48% of the final volume was present in mix 1 and 52% of the final volume was present in mix 2. The components were added in the following order to the reaction tubes at room temperature; 12.5 μl of Master Mix 1, 0.5 μl of the SSB or SSB Storage Buffer when performing controls, and 12 μl of Master Mix 2.

The 10×PCR buffer consisted of 100 mM Tris-HCl (pH 8.6), 500 mM KCl, and 15 mM $MgCl_2$. The 25 mM dNTP mixture contained the four deoxyribonucleotides that are required for DNA synthesis (dATP, dGTP, dTTP, and dCTP). Wild-type T7 SSB was prepared as described elsewhere herein except the final storage buffer was changed to 20 mM Tris-HCl (pH 8.5), 200 mM KCl, 1 mM DTT, 0.1 mM EDTA, 0.5% Tween-20, and 50% glycerol. Serial dilutions of the wild-type T7 SSB were performed in final storage buffer in order to add 0.5 μl per reaction. For control reactions without SSB, the SSB storage buffer, without any SSBs, was added instead. SSB was added to the reaction mixture before the primers and template. Taq DNA Polymerase was from USB Corporation, Cleveland, Ohio.

Each reaction contained 5 picomoles (pmol) of each primer and therefore a relatively simple calculation could be performed to determine the molar amount of single-stranded DNA binding sites in the reaction. Since the primers were each 25 bases in length and T7 SSB binds about 7 nucleotides per protein monomer, each primer had about 3.57 binding sites. Given there were 10 pmol total primers in each reaction×3.57 binding sites per primer meant there were roughly 36 pmol total ssDNA binding sites in each reaction. The mass amount of wild-type T7 SSB varied in this experiment, serially-doubling from 62.5 ng per reaction to 2 μg per reaction. Given the molecular weight of T7 SSB is 25,562 gm per mol per monomer, the following Table 8 could be constructed showing the molar amount of T7 SSB monomers in each reaction condition as well as the molar ratio of T7 SSB to total available binding sites in each reaction condition.

TABLE 8

| Mass amount of T7 SSB | Molar amount of monomers | Molar ratio of monomer:ssDNA |
| --- | --- | --- |
| 62.5 ng | 2.44 pmol | 0.068 |
| 125 ng | 4.89 pmol | 0.137 |
| 250 ng | 9.78 pmol | 0.274 |
| 500 ng | 19.56 pmol | 0.548 |
| 1 μg | 39.12 pmol | 1.096 |
| 2 μg | 78.24 pmol | 2.192 |

From Table 8, it is clear that the lowest concentration of T7 SSB (62.5 ng) in any reaction was an order of magnitude less than the molar amount of available binding sites in the reaction. The transition point from the lowest concentration of T7 SSB to one in which the molar ratio was equivalent occurred around 1 μg of T7 SSB. Thus, for primers 25 bases in length and at 5 pmol each in the reaction, concentrations of T7 SSB that were greater than 1 μg per reaction were in molar excess over the available ssDNA binding sites; as will be seen these were preferred conditions. It is noted that the molar ratios of T7 SSB (or any SSB with a known molecular weight) to available binding sites can be determined for a variety of primers of differing lengths and concentrations through these relatively straightforward calculations.

After all the reaction mixtures were completely assembled, the reaction tubes were placed in a thermal cycler (MJ Research, Waltham, Mass.) using the cycling conditions as listed below in Table 9. It is noted that an additional pre-incubation step at 25° C. for one hour was programmed into the thermal cycler so as to simulate room temperature. This extra time at 25° C. was chosen so as to favor the generation of nonspecific products.

TABLE 9

| Step | Temperature | Time |
| --- | --- | --- |
| Initial Soak | 25° C. | 60 minutes |
| Initial Denaturation | 95° C. | 2 minutes |
| Denaturation | 95° C. | 10 seconds |
| Hybridization | 60° C. | 5 seconds |
| Extension | 72° C. | 30 seconds |
| Repeat previous three steps 35 times | | |
| Final Extension | 72° C. | 5 minutes |
| Final Soak | 10° C. | as necessary |

Following cycling, 10 μl from each of the polymerase chain reactions were electrophoresed on a 1.5% TAE agarose gel containing ethidium bromide run at 100-120 volts for about 1-2 hours in 1×TAE buffer. The primer extension reaction products were visualized using a fluorescent scanner (Hitachi FMBIO II, San Francisco, Calif.).

The results of the foregoing reactions are shown in FIG. 4, wherein the numbered lanes correspond to the like-numbered Reactions described above and the Marker Lane, M, was provided using 1 Kb Plus DNA Ladder from Invitrogen Corporation, Carlsbad, Calif.

As is shown in FIG. 4, wild-type T7 SSB markedly enhanced the yield of the specific product. There is a clear concentration effect in which increasing concentrations of SSB yielded not only more specific product but fewer primer-dimers. This was exemplified by the reaction shown in lane 7 which had the lowest amount of primer-dimers and the highest amount of specific product relative to the control reaction without SSB (lane 1). This concentration effect was consistent with the stoichiometry predictions previously described. In reactions in which molar ratios of SSB monomers to available ssDNA binding sites was significantly less than one (lanes 2-4) less specific product was generated. In reactions in which molar ratios of SSB monomers to available ssDNA binding sites was close to or greater than one (lanes 5-7), more specific product was generated. Thus, although a range of concentrations of SSB are effective at increasing specific product yield, those concentrations that are equal to or exceed the molar concentration of primers in the reaction are most preferred.

One advantage of the primer sequestration method described herein is that it will work with any polymerase because the SSB interacts with and acts to inhibit the primers, and does not depend on any interaction with a particular polymerase. The antibody and chemical methods discussed in the BACKGROUND section require modifications to individual polymerases. There are at least 10 different polymerases commonly used for PCR, and thus the present invention has much broader utility. Furthermore, like those other methods, the methods disclosed herein permit the complete reaction system, including all of the reagents necessary to carry out multiple cycles of hybridization and primer extension reactions, to be completely assembled at nonstringent temperatures (such as room temperature), without the need to subsequently add a polymerase or any other component to the reaction mixture, thus risking contamination of the reactions.

As noted above, while the foregoing description has been provided in the context of performing a polymerase chain reaction, the invention is not to be limited to PCR. SSBs can be incorporated into other reaction mixtures for duplicating a template nucleic acid via primer-template hybridization and extension reactions to inhibit or prevent nonspecific primer extension products where it is convenient to combine all the components necessary for both reactions at nonstringent temperatures.

Also provided is a storage buffer solution useful for long-term storage of the SSBs useful in the disclosed methods (preferably up to one year) so that they do not lose their functional activity; i.e., their ability to effectively sequester primers or prevent or inhibit the generation of nonspecific primer extension products according to methods described herein. The storage buffer solution preferably has the following components listed in Table 10. It is noted that in Table 10, any concentration or range for any one component can be combined with any concentration or range for any other component to provide the buffer solution; it is not necessary that all concentrations or ranges come from the same column.

TABLE 10

Buffer solution for storage of SSB

| Component | Preferred | Less Preferred |
| --- | --- | --- |
| Tris HCl, pH 7.5 | 20 mM | 1-100 mM |
| | | 5-80 mM |
| | | 10-60 mM |
| | | 15-40 mM |
| EDTA | 1 mM | 1-100 mM |
| | | 1-50 mM |
| | | 1-10 mM |
| DTT | 0.5 mM | 0.005-200 mM |
| | | 0.01-100 mM |
| | | 0.02-50 mM |
| | | 0.03-25 mM |
| | | 0.04-10 mM |

TABLE 10-continued

Buffer solution for storage of SSB

| Component | Preferred | Less Preferred |
| --- | --- | --- |
| Salt (pref. NaCl) | 10 mM | 5-80 mM |
| | | 8-60 mM |
| | | 10-50 mM |
| | | 10-20 mM |
| | | 0 mM (for particular embodiment, explained below) |
| Glycerol | 50 mass percent | 10 to 80 mass percent |
| | | 20 to 70 mass percent |
| | | 30 to 60 mass percent |
| Water | Balance | Balance |

A suitable storage buffer can be prepared for, e.g., wild-type T7 gp2.5 using no salt, i.e., no sodium chloride. This was a particularly surprising and unexpected result, as it ordinarily would have been expected that to prevent the SSB from precipitating out of solution, a quantity of salt, such as sodium chloride, would be required. Generally, it is preferred nevertheless to provide the buffer solution with 10 mM salt concentration. For the T7 gp2.5-Δ21C mutant disclosed above, a somewhat higher salt concentration is desirable to sustain the mutant in solution (i.e., prevent its precipitation), and preferably greater than 50 mM salt concentration is used.

To perform a PCR amplification procedure using the SSB in its storage buffer, an aliquot of the SSB in its storage buffer is extracted, as by pipette, from the buffer solution container and then delivered to the PCR reaction vessel or tube when preparing the PCR reaction mixture, typically at room temperature. It has been found that the buffer solution disclosed above does not adversely affect the PCR amplification mechanism, and that suitable amplification results are obtained using a variety of different polymerases, e.g., with wild-type Taq DNA polymerase and a mutant variant of Taq DNA polymerase as well as Pfu DNA polymerase.

Thus, the buffer solution disclosed herein has the advantages the SSBs remain stable and functionally active (capable to inhibit primer hybridization at non-stringent temperatures) when stored therein for extended periods, preferably at least 1, 2, 3, 4, 5, 6, 7, 8, 9, 10, 11 or 12, months, and the residual storage buffer solution that is delivered to the PCR reaction tube along with the SSBs does not adversely affect PCR amplification reactions when using a range of polymerases.

Preferably, a liquid formulation composed of an SSB, e.g., wild-type T7gp2.5, in a buffer solution as described above has a total protein concentration ranging from 1 μg/ml to 200 mg/ml, more preferably 10 μg/ml to 100 mg/ml, even more preferably 100 μg/ml to 50 mg/ml and most preferably between 1 mg and 5 mg/ml. In addition, other single-stranded nucleic acid binding proteins involved or not involved in replication mechanism such as but not limited to the following SSBs can be used in combination with or in place of wild-type T7gp2.5: T7gp2.5-F232L, T7 gp2.5-Δ21C, T4 gp32, Rec A, λ beta protein, etc. In a preferred embodiment, the resulting formulation of wild-type T7 gp2.5 (or other) binding protein in the above-described storage buffer has a pH between 4.0 and 12.0, more preferably between pH 6.0 and 10.0, even more preferably between 7.0 and 9.0 and most preferably pH 7.5±0.2. Table 11 below describes preferred compositions for a formulation of SSB in a storage buffer which can include further or additional additives or components beyond those described above.

TABLE 11

Compositions for SSB formulations in storage buffer

| Component/Property | Most preferred concentration/value | More Preferably | Preferably | Less Preferably |
|---|---|---|---|---|
| SSB (preferably T7gp2.5, wild-type or mutant variant) | 1-5 mg/ml | 100 μg-50 mg/ml | 10 μg-100 mg/ml | 1 μg-200 mg/ml |
| pH | 7.5 ± 0.2 | 7.0-9.0 | 6.0-10.0 | 4.0-12.0 |
| Buffer such as MOPS, HEPES, TRICINE, etc | 20 mM ± 5 mM Tris-HCl pH 7.5 to pH 8.5 | 15-50 mM | 5-100 mM | 0-250 mM |
| Reducing Agent (DTT or β-ME) | 1 ± 0.2 mM | 0.5-10 mM | 0.1-50 mM | 0-100 mM |
| Monovalent Ions ($Na^+$, $K^+$, $Li^+$, $Cl^-$ etc.) | 10 ± 2 mM | 1-100 mM | 0.5-200 mM | 0-500 mM |
| Complexing/Chelating Agent such as EDTA, EGTA, etc. | 0.5 mM ± 0.1 mM | 0.1-1 mM | 0.01-2 mM | 0-100 mM |
| Divalent Ions ($Zn^{2+}$, $Mg^{2+}$, $Co^{2+}$, etc.) | 0-50 mM | 0-100 mM | 0-200 mM | 0-500 mM |
| Amino Acid Based Carrier such as Bovine Serum Albumine, Poly L-lysine, etc. | | 0-1 mg/ml | 0-10 mg/ml | 0-100 mg/ml |
| Non ionic Detergents such as Nonidet P40, Triton X100, Tween 20, etc. | | 0.1%-1% (v/v) | 0.01%-5% (v/v) | 0-20% (v/v) |
| Zwitterionic Detergents such as CHAPS or CHAPSO | | 0.1%-1% (v/v) | 0.01%-5% (v/v) | 0-20% (v/v) |
| Ionic Detergents such as SDS | | 0.005%-0.1% (v/v) | 0.0001%-1% (v/v) | 0-5% (v/v) |
| DMSO | | 0.01%-1% (v/v) | 0.001%-10% (v/v) | 0-50% (v/v) |
| Polysaccharide/Dextran | | 1%-5% (v/v) | 0.1%-10% (v/v) | 0-50% (v/v) |
| Protein Stabilizer such as glycerol, Ethylene glycol, etc. | 50% ± 5% (v/v) | 5%-65% (v/v) | 1%-75% (v/v) | 0-99% (v/v) |
| Mono or disaccharide such as glucose, maltose, etc. | | 10-10,000× Protein mass | 1-100× Protein mass | 0.1-10× protein mass |

Although the hereinabove described embodiments constitute preferred embodiments of the invention, it is to be understood that various modifications or changes can be made thereto without departing from the spirit and the scope of the invention as set forth in the appended claims.

What is claimed is:

1. A PCR reaction mixture that is at a temperature below 37° C., said mixture comprising a template nucleic acid, a primer having a nucleotide sequence that is complementary to a specific target portion of said template nucleic acid, an enzyme effective to catalyze primer extension, nucleotides necessary for enzyme-directed nucleic acid synthesis, and a single-stranded nucleic acid binding protein effective to inhibit said primer from participating in a primer extension reaction up to at least a first temperature at or below 30° C., wherein the inhibitive capability of said single-stranded nucleic acid binding protein is lost via denaturation thereof at a second temperature in the range of 50° C. to about 72° C. as a result of being subjected to said second temperature, said template nucleic acid being unamplified and not denatured, said single-stranded nucleic acid binding protein being present in said reaction mixture in a stoichiometric excess relative to said primer.

2. A PCR reaction mixture according to claim 1, said single-stranded nucleic acid binding protein comprising at least one of wild-type T7 gp2.5 and its mutant variants, or a combination thereof.

3. A PCR reaction mixture according to claim 1, said single-stranded nucleic acid binding protein comprising at least one of T7gp2.5-F232L and T7 gp2.5-Δ21C.

4. A PCR reaction mixture according to claim 1, said single-stranded nucleic acid binding protein comprising a mixture of proteins including wild-type T7 gp2.5 and T7gp2.5-Δ26C.

5. A PCR reaction mixture according to claim 1, said stoichiometric excess being at least 2-fold.

6. A PCR reaction mixture according to claim 1, said stoichiometric excess being at least 3-fold.

7. A PCR reaction mixture according to claim 1, said stoichiometric excess being at least 4-fold.

8. A PCR reaction mixture according to claim 1, said stoichiometric excess being at least 50%.

9. A PCR reaction mixture according to claim 1, said stoichiometric excess being at least 1-fold.

* * * * *

UNITED STATES PATENT AND TRADEMARK OFFICE
CERTIFICATE OF CORRECTION

| | |
|---|---|
| PATENT NO. | : 7,951,534 B2 |
| APPLICATION NO. | : 11/939820 |
| DATED | : May 31, 2011 |
| INVENTOR(S) | : Christopher James Kubu, Jeannine Catherine Muller-Greven and Robert Bruce Moffett |

It is certified that error appears in the above-identified patent and that said Letters Patent is hereby corrected as shown below:

At Col. 12, Line 67, replace "$\delta$" with "a".

Signed and Sealed this
Twenty-ninth Day of November, 2011

David J. Kappos
*Director of the United States Patent and Trademark Office*

```
                          SEQUENCE LISTING

<160> NUMBER OF SEQ ID NOS: 15

<210> SEQ ID NO 1
<211> LENGTH: 33
<212> TYPE: DNA
<213> ORGANISM: Artificial Sequence
<220> FEATURE:
<223> OTHER INFORMATION: Forward PCR amplification primer for
      Bacteriophage T7 gp2.5

<400> SEQUENCE: 1
atccatatgg ctaagaagat tttcacctct gcg                              33

<210> SEQ ID NO 2
<211> LENGTH: 40
<212> TYPE: DNA
<213> ORGANISM: Artificial Sequence
<220> FEATURE:
<223> OTHER INFORMATION: Reverse PCR amplification primer for
      Bacteriophage T7 gp2.5

<400> SEQUENCE: 2 gtcgacccccg ggttagaagt cgccgtcttc gtctgcttcc                      40

<210> SEQ ID NO 3
<211> LENGTH: 699
<212> TYPE: DNA
<213> ORGANISM: Bacteriophage T7
```

<400> SEQUENCE: 3

```
atggctaaga agattttcac ctctgcgctg ggtaccgctg aaccttacgc ttacatcgcc    60
aagccggact acggcaacga agagcgtggc tttgggaacc ctcgtggtgt ctataaagtt   120
gacctgacta ttcccaacaa agacccgcgc tgccagcgta tggtcgatga atcgtgaag   180
tgtcacgaag aggcttatgc tgctgccgtt gaggaatacg aagctaatcc acctgctgta   240
gctcgtggta agaaaccgct gaaaccgtat gagggtgaca tgccgttctt cgataacggt   300
gacggtacga ctacctttaa gttcaaatgc tacgcgtctt ccaagacaa gaagaccaaa   360
gagaccaagc acatcaatct ggttgtggtt gactcaaaag gtaagaagat ggaagacgtt   420
ccgattatcg gtggtggctc taagctgaaa gttaaatatt ctctggttcc atacaagtgg   480
aacactgctg taggtgcgag cgttaagctg caactggaat ccgtgatgct ggtcgaactg   540
gctacctttg gtggcggtga agacgattgg gctgacgaag ttgaagagaa cggctatgtt   600
gcctctggtt ctgccaaagc gagcaaacca cgcgacgaag aaagctggga cgaagacgac   660
gaagagtccg aggaagcaga cgaagacggc gacttctaa                         699
```

<210> SEQ ID NO 4
<211> LENGTH: 232
<212> TYPE: PRT
<213> ORGANISM: Bacteriophage T7

<400> SEQUENCE: 4

```
Met Ala Lys Lys Ile Phe Thr Ser Ala Leu Gly Thr Ala Glu Pro Tyr
1               5                   10                  15

Ala Tyr Ile Ala Lys Pro Asp Tyr Gly Asn Glu Glu Arg Gly Phe Gly
            20                  25                  30

Asn Pro Arg Gly Val Tyr Lys Val Asp Leu Thr Ile Pro Asn Lys Asp
        35                  40                  45

Pro Arg Cys Gln Arg Met Val Asp Glu Ile Val Lys Cys His Glu Glu
    50                  55                  60

Ala Tyr Ala Ala Ala Val Glu Glu Tyr Glu Ala Asn Pro Pro Ala Val
65                  70                  75                  80

Ala Arg Gly Lys Lys Pro Leu Lys Pro Tyr Glu Gly Asp Met Pro Phe
                85                  90                  95

Phe Asp Asn Gly Asp Gly Thr Thr Thr Phe Lys Phe Lys Cys Tyr Ala
            100                 105                 110

Ser Phe Gln Asp Lys Lys Thr Lys Glu Thr Lys His Ile Asn Leu Val
        115                 120                 125

Val Val Asp Ser Lys Gly Lys Lys Met Glu Asp Val Pro Ile Ile Gly
    130                 135                 140

Gly Gly Ser Lys Leu Lys Val Lys Tyr Ser Leu Val Pro Tyr Lys Trp
145                 150                 155                 160

Asn Thr Ala Val Gly Ala Ser Val Lys Leu Gln Leu Glu Ser Val Met
                165                 170                 175

Leu Val Glu Leu Ala Thr Phe Gly Gly Gly Glu Asp Asp Trp Ala Asp
            180                 185                 190

Glu Val Glu Glu Asn Gly Tyr Val Ala Ser Gly Ser Ala Lys Ala Ser
        195                 200                 205

Lys Pro Arg Asp Glu Glu Ser Trp Asp Glu Asp Glu Glu Ser Glu
    210                 215                 220

Glu Ala Asp Glu Asp Gly Asp Phe
225                 230
```

-continued

```
<210> SEQ ID NO 5
<211> LENGTH: 211
<212> TYPE: PRT
<213> ORGANISM: Artificial Sequence
<220> FEATURE:
<223> OTHER INFORMATION: T7 gp2.5-delta21C mutant

<400> SEQUENCE: 5

Met Ala Lys Lys Ile Phe Thr Ser Ala Leu Gly Thr Ala Glu Pro Tyr
 1               5                  10                  15

Ala Tyr Ile Ala Lys Pro Asp Tyr Gly Asn Glu Glu Arg Gly Phe Gly
             20                  25                  30

Asn Pro Arg Gly Val Tyr Lys Val Asp Leu Thr Ile Pro Asn Lys Asp
         35                  40                  45

Pro Arg Cys Gln Arg Met Val Asp Glu Ile Val Lys Cys His Glu Glu
     50                  55                  60

Ala Tyr Ala Ala Val Glu Glu Tyr Glu Ala Asn Pro Pro Ala Val
 65                  70                  75                  80

Ala Arg Gly Lys Lys Pro Leu Lys Pro Tyr Glu Gly Asp Met Pro Phe
                 85                  90                  95

Phe Asp Asn Gly Asp Gly Thr Thr Thr Phe Lys Phe Lys Cys Tyr Ala
            100                 105                 110

Ser Phe Gln Asp Lys Lys Thr Lys Glu Thr Lys His Ile Asn Leu Val
        115                 120                 125

Val Val Asp Ser Lys Gly Lys Lys Met Glu Asp Val Pro Ile Ile Gly
    130                 135                 140

Gly Gly Ser Lys Leu Lys Val Lys Tyr Ser Leu Val Pro Tyr Lys Trp
145                 150                 155                 160

Asn Thr Ala Val Gly Ala Ser Val Lys Leu Gln Leu Glu Ser Val Met
                165                 170                 175

Leu Val Glu Leu Ala Thr Phe Gly Gly Gly Asp Asp Trp Ala Asp
            180                 185                 190

Glu Val Glu Glu Asn Gly Tyr Val Ala Ser Gly Ser Ala Lys Ala Ser
        195                 200                 205

Lys Pro Arg
    210

<210> SEQ ID NO 6
<211> LENGTH: 206
<212> TYPE: PRT
<213> ORGANISM: Artificial Sequence
<220> FEATURE:
<223> OTHER INFORMATION: T7 gp2.5-delta26C mutant

<400> SEQUENCE: 6

Met Ala Lys Lys Ile Phe Thr Ser Ala Leu Gly Thr Ala Glu Pro Tyr
 1               5                  10                  15

Ala Tyr Ile Ala Lys Pro Asp Tyr Gly Asn Glu Glu Arg Gly Phe Gly
             20                  25                  30

Asn Pro Arg Gly Val Tyr Lys Val Asp Leu Thr Ile Pro Asn Lys Asp
         35                  40                  45

Pro Arg Cys Gln Arg Met Val Asp Glu Ile Val Lys Cys His Glu Glu
     50                  55                  60

Ala Tyr Ala Ala Val Glu Glu Tyr Glu Ala Asn Pro Pro Ala Val
 65                  70                  75                  80

Ala Arg Gly Lys Lys Pro Leu Lys Pro Tyr Glu Gly Asp Met Pro Phe
                 85                  90                  95
```

```
Phe Asp Asn Gly Asp Gly Thr Thr Thr Phe Lys Phe Lys Cys Tyr Ala
            100                 105                 110

Ser Phe Gln Asp Lys Lys Thr Lys Glu Thr Lys His Ile Asn Leu Val
        115                 120                 125

Val Val Asp Ser Lys Gly Lys Lys Met Glu Asp Val Pro Ile Ile Gly
    130                 135                 140

Gly Gly Ser Lys Leu Lys Val Lys Tyr Ser Leu Val Pro Tyr Lys Trp
145                 150                 155                 160

Asn Thr Ala Val Gly Ala Ser Val Lys Leu Gln Leu Glu Ser Val Met
                165                 170                 175

Leu Val Glu Leu Ala Thr Phe Gly Gly Gly Glu Asp Asp Trp Ala Asp
            180                 185                 190

Glu Val Glu Glu Asn Gly Tyr Val Ala Ser Gly Ser Ala Lys
        195                 200                 205
```

```
<210> SEQ ID NO 7
<211> LENGTH: 232
<212> TYPE: PRT
<213> ORGANISM: Artificial Sequence
<220> FEATURE:
<223> OTHER INFORMATION: T7 gp2.5-F232L mutant

<400> SEQUENCE: 7

Met Ala Lys Lys Ile Phe Thr Ser Ala Leu Gly Thr Ala Glu Pro Tyr
1               5                   10                  15

Ala Tyr Ile Ala Lys Pro Asp Tyr Gly Asn Glu Glu Arg Gly Phe Gly
            20                  25                  30

Asn Pro Arg Gly Val Tyr Lys Val Asp Leu Thr Ile Pro Asn Lys Asp
        35                  40                  45

Pro Arg Cys Gln Arg Met Val Asp Glu Ile Val Lys Cys His Glu Glu
    50                  55                  60

Ala Tyr Ala Ala Ala Val Glu Glu Tyr Glu Ala Asn Pro Pro Ala Val
65                  70                  75                  80

Ala Arg Gly Lys Lys Pro Leu Lys Pro Tyr Glu Gly Asp Met Pro Phe
                85                  90                  95

Phe Asp Asn Gly Asp Gly Thr Thr Thr Phe Lys Phe Lys Cys Tyr Ala
            100                 105                 110

Ser Phe Gln Asp Lys Lys Thr Lys Glu Thr Lys His Ile Asn Leu Val
        115                 120                 125

Val Val Asp Ser Lys Gly Lys Lys Met Glu Asp Val Pro Ile Ile Gly
    130                 135                 140

Gly Gly Ser Lys Leu Lys Val Lys Tyr Ser Leu Val Pro Tyr Lys Trp
145                 150                 155                 160

Asn Thr Ala Val Gly Ala Ser Val Lys Leu Gln Leu Glu Ser Val Met
                165                 170                 175

Leu Val Glu Leu Ala Thr Phe Gly Gly Gly Glu Asp Asp Trp Ala Asp
            180                 185                 190

Glu Val Glu Glu Asn Gly Tyr Val Ala Ser Gly Ser Ala Lys Ala Ser
        195                 200                 205

Lys Pro Arg Asp Glu Glu Ser Trp Asp Glu Asp Glu Glu Ser Glu
    210                 215                 220

Glu Ala Asp Glu Asp Gly Asp Leu
225                 230

<210> SEQ ID NO 8
<211> LENGTH: 306
<212> TYPE: DNA
```

<213> ORGANISM: Human

<400> SEQUENCE: 8

```
gaggttccta caggcacctg cccagtggat ccttttgaag cccagtgggc tgcattagaa    60
aataagtcca agcagcgtac taatccctcc cctaccaacc ctttctccag tgacttacag   120
aagacgtttg aaattgaact ttaagcaatc attatggcta tgtatcttgt ccataccaga   180
cagggagcag ggggtagcgg tcaaaggagc aaaacagact ttgtctcctg attagtactc   240
ttttcactaa tcccaaaggt cccaaggaac aagtccaggc ccagagtact gtgaggggtg   300
attttg                                                              306
```

<210> SEQ ID NO 9
<211> LENGTH: 25
<212> TYPE: DNA
<213> ORGANISM: Artificial Sequence
<220> FEATURE:
<223> OTHER INFORMATION: Forward PCR amplification primer for 306-base pair region of gene Numb of human genomic DNA

<400> SEQUENCE: 9

```
gaggttccta caggcacctg cccag                                          25
```

<210> SEQ ID NO 10
<211> LENGTH: 25
<212> TYPE: DNA
<213> ORGANISM: Artificial Sequence
<220> FEATURE:
<223> OTHER INFORMATION: Reverse PCR amplification primer for 306-base pair region of gene Numb of human genomic DNA

<400> SEQUENCE: 10

```
caaaatcacc cctcacagta ctctg                                          25
```

<210> SEQ ID NO 11
<211> LENGTH: 1142
<212> TYPE: DNA
<213> ORGANISM: Human

<400> SEQUENCE: 11

```
tgctttatct gttcacttgt gccctgactt tcaactctgt ctccttcctc ttcctacagt    60
actcccctgc cctcaacaag atgttttgcc aactggccaa gacctgccct gtgcagctgt   120
gggttgattc cacaccccg cccggcaccc gcgtccgcgc catggccatc tacaagcagt   180
cacagcacat gacggaggtt gtgaggcgct gccccccacca tgagcgctgc tcagatagcg   240
atggtgagca gctggggctg gagagacgac agggctggtt gcccagggtc cccaggcctc   300
tgattcctca ctgattgctc ttaggtctgg cccctcctca gcatcttatc cgagtggaag   360
gaaatttgcg tgtggagtat ttggatgaca gaaacacttt tcgacatagt gtggtggtgc   420
cctatgagcc gctgaggtc tggttttgcaa ctggggtctc tggaggagg ggttaagggt   480
ggttgtcagt ggccctccag gtgagcagta gggggctttt ctcctgctgc ttatttgacc   540
tccctataac cccatgagat gtgcaaagta aatgggttta actattgcac agttgaaaaa   600
actgaagctt acagaggcta agggcctccc ctgcttggct gggcgcagtg gctcatgcct   660
gtaatcccag cactttggga ggccaaggca ggcggatcac gaggtggga gatcgagacc   720
atcctggcta acggtgaaac cccgtctcta ctgaaaaata caaaaaaaaa ttagccgggc   780
gtggtgctgg gcacctgtag tcccagctac tcgggaggct gaggaaggag aatggcgtga   840
acctgggcgg tggagcttgc agtgagctga gatcacgcca ctgcactcca gcctgggcga   900
```

```
cagagcgaga ttccatctca aaaaaaaaaa aaaaaggcct ccsctgcttg ccacaggtct    960
ccccaaggcg cactggcctc atcttgggcc tgtgttatct cctaggttgg ctctgactgt   1020
accaccatcc actacaacta catgtgtaac agttcctgca tgggcggcat gaaccggagg   1080
cccatcctca ccatcatcac actggaagac tccaggtcag gagccacttg ccaccctgca   1140
ca                                                                  1142

<210> SEQ ID NO 12
<211> LENGTH: 24
<212> TYPE: DNA
<213> ORGANISM: Artificial Sequence
<220> FEATURE:
<223> OTHER INFORMATION: Forward PCR amplification primer for 1142-base
      pair region of gene p53 of human genomic DNA

<400> SEQUENCE: 12
tgctttatct gttcacttgt gccc                                            24

<210> SEQ ID NO 13
<211> LENGTH: 20
<212> TYPE: DNA
<213> ORGANISM: Artificial Sequence
<220> FEATURE:
<223> OTHER INFORMATION: Reverse PCR amplification primer for 1142-base
      pair region of gene p53 of human genomic DNA

<400> SEQUENCE: 13
tgtgcagggt ggcaagtggc                                                 20

<210> SEQ ID NO 14
<211> LENGTH: 23
<212> TYPE: DNA
<213> ORGANISM: Artificial Sequence
<220> FEATURE:
<223> OTHER INFORMATION: Forward PCR amplification primer for "mock"
      amplification reaction of Example 3, wherein HEX fluorescent label
      is attached to 5' d-cytosine

<400> SEQUENCE: 14
cttttcccag tcacgacgtt gta                                             23

<210> SEQ ID NO 15
<211> LENGTH: 41
<212> TYPE: DNA
<213> ORGANISM: Artificial Sequence
<220> FEATURE:
<223> OTHER INFORMATION: Reverse PCR amplification primer for "mock"
      amplification reaction of Example 3

<400> SEQUENCE: 15
atgcaagctt ggcactggcc gtcgttttac aacgtcgtga c                         41
```